United States Patent [19]
Cigan et al.

[11] Patent Number: 6,057,491
[45] Date of Patent: May 2, 2000

[54] PROTEIN HAVING INSECTICIDAL ACTIVITIES AND METHOD OF USE

[75] Inventors: Amy L. Cigan, Des Moines; Thomas Czapla, Urbandale; Patricia Lynne Fallis, Polk City; Terry Meyer, Urbandale; Scott A. Mundell, West Des Moines; Brian T. Sabus, Johnston, all of Iowa; Karel R. Schubert, Norman, Okla.

[73] Assignees: Borad of Regents for University of Oklahoma, Norman, Okla.; Pioneer Hi-Bred International, Inc., Johnston, Iowa

[21] Appl. No.: 09/074,912

[22] Filed: May 8, 1998

Related U.S. Application Data

[60] Provisional application No. 60/047,864, May 29, 1997.

[51] Int. Cl.⁷ .............................. C12N 5/04; C12N 15/29; C12N 15/82; A01H 5/00; A01H 5/10
[52] U.S. Cl. .................... 800/279; 435/69.1; 435/320.1; 435/410; 435/412; 435/418; 435/419; 435/430; 435/468; 435/252.3; 435/254.11; 536/24.1; 536/23.6; 800/287; 800/298; 800/302; 800/320; 800/320.1
[58] Field of Search .................................... 435/69.1, 410, 435/412, 418, 419, 430, 468, 320.1, 252.3, 254.11; 536/24.1, 23.6; 800/278, 279, 287, 288, 298, 301, 302, 320, 320.1

[56] References Cited

U.S. PATENT DOCUMENTS 5,446,019  8/1995  Ely et al. .................................. 514/424

FOREIGN PATENT DOCUMENTS

| 2090552 | 8/1994 | WIPO | ............................ C12N 15/82 |
| WO 94/21805 | 9/1994 | WIPO | ............................ C12N 15/82 |
| WO 96/37615 | 11/1996 | WIPO | ............................ C12N 15/29 |
| WO 97/19109 | 5/1997 | WIPO | ............................ C07K 14/81 |
| WO 98/21244 | 5/1998 | WIPO | ............................ C07K 14/81 |

OTHER PUBLICATIONS

Wu et al, Mol. Breed., vol. 3, pp. 371–380, 1997.
Estruch et al, Nature Biotech., vol. 15, pp. 137–141, 1997.
Johnson, et al., "Expression of Proteinase Inhibitors I and II In Transgenic Tobacco Plants; Effects On Natural Defense Against *Manduca sexta* Larvae," Proc. Natl. Acad. Sci., vol. 86, Dec. 1989, pp. 9871–9875.
Chrispeels, et al., "Lectins, Lectin Genes, and Their Role In Plant Defense," The Plant Cell, vol. 3, Jan. 1991, pp. 1–9.
Ryan, "Protease Inhibitors In Plants: Genes For Improving Defenses Against Insects and Pathogens," Annu. Rev. Phytopathol, vol. 38, 1990, pp. 425–449.
Janzen, et al., "Potentially Defensive Proteins In Mature Seeds Of 59 Species Of Tropical Leguminosae," J. Chem. Ecol., vol. 12, 1986, pp. 1469–1480.
Janzen, et al., "Toxicity Of Secondary Compounds To The Seed–Eating Larvae Of The Bruchid Beetle *Callosobruchus Maculatus*," Phytochemistry, Vo. 16, 1977, pp. 223–227.
Czapla, et al., Effect Of Plant Lectins On The Larval Development Of European Corn Borer (Lepidoptera: Pyralidae) and Sourthern Corn Rootworm (Coleoptera: Chrysomelidae) J. Econ. Entomol., vol. 83, 1990, pp. 2480–2485.
Christeller, et al., "The Interaction Of A Range Of Serine Proteinase Inhibitors With Bovine Trypsin And *Costelytra Zealandica* Trypsin,"Insect Biochem., vol. 19, 1989, pp. 233–241.
Hammer, et al., "Trypsin Inhibitors From *Colocasia Esculenta, Alcasia Macrorrhiza* And *Cyrtosperma Chamissonis*, "Phytochemistry, vol. 28, 1989, pp. 3019–3026.
Chun, et al., "*Pentaclethra macroloba* Seed Effect On Larval Growth, Cell Viability, and Midgut Enzyme Activity of *Helicoverpa zea* (Lepidoptera: Noctuidae)," J. Econ. Entomol., vol. 87, Dec. 1994, pp. 1754–1760.
Hilder, et al., "A Novel Mechanism Of Insect Resistance Engineered Into Tobacco," Nature, vol. 330, Nov. 1987, pp. 160–163.
Chun et al., Pentaclethra macroloba Seed Effect on Larval Growth, Cell Viability and Midgut Enzyme Activity of *Helicoverpa zea* (Lepidoptera: Noctuidae), *J. Econ. Entomol.*, 86(6):1754–1760 (1994).
Reeck et al. Cell, vol. 50, p. 667, 1987.
Lewin, R., Science, vol. 237, p. 1570, 1987.

*Primary Examiner*—David T. Fox
*Assistant Examiner*—Ashwin D. Mehta
*Attorney, Agent, or Firm*—Alston & Bird LLP

[57] ABSTRACT

Compositions and methods for controlling pests, particularly insect pests, are provided. The compositions comprise proteins isolated from plants of the genus Pentaclethra. Nucleotide sequences encoding the proteins are also provided. Such sequences find use in transforming organisms for control of pests.

26 Claims, 11 Drawing Sheets

```
           CGGCACGAGCTCGTACAGATTCTATCCATTATGAAGTCGAAAATGGCCAT
        1  ---------+---------+---------+---------+---------+  50
a                                          M  K  S  K  M  A  M  -
b                                                               -
c                                                               -
        1  ---------+---------+---------+---------+---------+  50
d                                                               -
e                                                               -
f                                                               -

GCTCCTTTTGTTATTTTGTGTGTTATCTAATCAGCTAGTGGCAGCATTTT
       51  ---------+---------+---------+---------+---------+ 100
a           L  L  L  L  F  C  V  L  S  N  Q  L  V  A  A  F  S  -
b                                                               -
c                                                               -
       51  ---------+---------+---------+---------+---------+ 100
d                                                               -
e                                                               -
f                                                               -

CCACACAAGCGAAAGCTTCTAAAGATGGAAACTTAGTCACAGTTCTTGCC
      101  ---------+---------+---------+---------+---------+ 150
a              T  Q  A  K  A  S  K  D  G  N  L  V  T  V  L  A  -
b                                                               -
c                                                               -
      101  ---------+---------+---------+---------+---------+ 150
d                                                               -
e                                                               -
f                                                               -

ATTGATGGAGGTGGTATCAGAGGAATTATCCCCGGAGTTATTCTCAAACA
      151  ---------+---------+---------+---------+---------+ 200
a           I  D  G  G  G  I  R  G  I  I  P  G  V  I  L  K  Q  -
b                                                               -
c                                                               -
      151  ---------+---------+---------+---------+---------+ 200
d                                                               -
e                                                               -
f                                                               -

ACTAGAAGCTACTCTTCAGAGATGGGACTCAAGTGCAAGACTAGCAGAGT
      201  ---------+---------+---------+---------+---------+ 250
a              L  E  A  T  L  Q  R  W  D  S  S  A  R  L  A  E  Y -
b                                                                 -
c                                                                 -
```

ATTTTGATGTGGTTGCCGGGACGAGCACTGGAGGGATTATAACTGCCATT
      251 ----------+---------+---------+---------+---------+ 300
    a        F   D   V   V   A   G   T   S   T   G   G   I   I   T   A   I
    b                                                          -
    c
      251 ----------+---------+---------+---------+---------+ 300
    d
    e
    f                                                          -

CTAACTGCCCCGGACCCACAAAACAAGGACCGTCCTTTGTATGCTGCCGA
      301 ----------+---------+---------+---------+---------+ 350
    a        L   T   A   P   D   P   Q   N   K   D   R   P   L   Y   A   A   E
    b                                                          -
    c
      301 ----------+---------+---------+---------+---------+ 350
    d
    e
    f                                                          -

AGAAATTATCGACTTCTACATAGAGCATGGTCCTTCCATTTTTAATAAAT
      351 ----------+---------+---------+---------+---------+ 400
    a        E   I   I   D   F   Y   I   E   H   G   P   S   I   F   N   K   S
    b                                                          -
    c
      351 ----------+---------+---------+---------+---------+ 400
    d
    e
    f                                                          -

CCACCGCCTGCTCGTTGCCTGGTATCTTTTGTCCAAAGTATGATGGGAAG
      401 ----------+---------+---------+---------+---------+ 450
    a        T   A   C   S   L   P   G   I   F   C   P   K   Y   D   G   K
    b                                                          -
    c
      401 ----------+---------+---------+---------+---------+ 450
    d
    e
    f                                                          -

TATTTACAAGAAATAATAAGCCAGAAATTGAATGAAACACTACTAGACCA
      451 ----------+---------+---------+---------+---------+ 500
    a        Y   L   Q   E   I   I   S   Q   K   L   N   E   T   L   L   D   Q
    b                                                          -
    c
      451 ----------+---------+---------+---------+---------+ 500
    d
    e
    f                                                          -
```

Figure 1B

```
            GACAACAACAAATGTTGTTATCCCTTCCTTCGACATCAAGCTTCTTCGTC
     501    ---------+---------+---------+---------+---------+  550
  a          T  T  T  N  V  V  I  P  S  F  D  I  K  L  L  R  P   -
  b                                                               -
  c                                                               -
     501    ---------+---------+---------+---------+---------+  550
  d                                                               -
  e                                                               -
  f                                                               -

CAACCATATTCTCAACTTTCAAGTTAGAGGAAGTTCCTGAGTTAAATGTC
     551    ---------+---------+---------+---------+---------+  600
  a           T  I  F  S  T  F  K  L  E  E  V  P  E  L  N  V     -
  b                                                               -
  c                                                               -
     551    ---------+---------+---------+---------+---------+  600
  d                                                               -
  e                                                               -
  f                                                               -

AAACTCTCCGATGTATGCATGGGAACTTCAGCAGCACCAATCGTATTTCC
     601    ---------+---------+---------+---------+---------+  650
  a          K  L  S  D  V  C  M  G  T  S  A  A  P  I  V  F  P   -
  b                                                               -
  c                                                               -
     601    ---------+---------+---------+---------+---------+  650
  d                                                               -
  e                                                               -
  f                                                               -

TCCCTATTATTTCAAGCATGGAGATACTGAATTCAATCTCGTTGATGGTG
     651    ---------+---------+---------+---------+---------+  700
  a           P  Y  Y  F  K  H  G  D  T  E  F  N  L  V  D  G  A  -
  b                                                               -
  c                                                               -
     651    ---------+---------+---------+---------+---------+  700
  d                                                               -
  e                                                               -
  f                                                               -

CAATCATCGCTGATATTCCGGCCCCGGTTGCTCTCAGCGAGGTGCTCCAG
     701    ---------+---------+---------+---------+---------+  750
  a           I  I  A  D  I  P  A  P  V  A  L  S  E  V  L  Q     -
  b                                                               -
  c                                                               -
     701    ---------+---------+---------+---------+---------+  750
  d                                                               -
  e                                                               -
  f                                                               -

CAAGAAAAATACAAGAATAAAGAAATCCTTTTGCTGTCTATAGGAACTGG
     751    ---------+---------+---------+---------+---------+  800
  a          Q  E  K  Y  K  N  K  E  I  L  L  L  S  I  G  T  G   -
  b                                                               -
```

Figure 1C

```
c                                                                           -
      751 ---------+---------+---------+---------+---------+ 800
d                                                                           -
e                                                                           -
f                                                                           -
          AGTTGTAAAACCTGGTGAGGGTTATTCTGCTAATCGTACTTGGACTATTT
      801 ---------+---------+---------+---------+---------+ 850
a            V   V   K   P   G   E   G   Y   S   A   N   R   T   W   I   F  -
b                                                                           -
c                                                                           -
      801 ---------+---------+---------+---------+---------+ 850
d                                                                           -
e                                                                           -
f                                                                           -
          TCGATTGGAGTAGTGAAACTTTAATCGGGCTTATGGGTCATGGAACGAGA
      851 ---------+---------+---------+---------+---------+ 900
a            D   W   S   S   E   T   L   I   G   L   M   G   H   G   T   R  -
b                                                                           -
c                                                                           -
      851 ---------+---------+---------+---------+---------+ 900
d                                                                           -
e                                                                           -
f                                                                           -
          GCCATGTCTGATTATTACGTTGGCTCACATTTCAAAGCCCTTCAACCCCA
      901 ---------+---------+---------+---------+---------+ 950
a            A   M   S   D   Y   Y   V   G   S   H   F   K   A   L   Q   P   Q -
b                                                                           -
c                                                                           -
      901 ---------+---------+---------+---------+---------+ 950
d                                                                           -
e                                                                           -
f                                                                           -
          GAATAACTACCTCCGAATTCAGGAATACGATTTAGATCCGGCACTGGAAA
      951 ---------+---------+---------+---------+---------+ 1000
a            N   N   Y   L   R   I   Q   E   Y   D   L   D   P   A   L   E   S -
b                                                                           -
c                                                                           -
      951 ---------+---------+---------+---------+---------+ 1000
d                                                                           -
e                                                                           -
f                                                                           -
          GCATTGATGATGCTTCAACGGAAAACATGGAGAATCTGGAAAAGGTAGGA
     1001 ---------+---------+---------+---------+---------+ 1050
a            I   D   D   A   S   T   E   N   M   E   N   L   E   K   V   G  -
b                                                                           -
c                                                                           -
     1001 ---------+---------+---------+---------+---------+ 1050
d                                                                           -
e                                                                           -
f                                                                           -
```

Figure 1D

```
              CAGAGTTTGTTGAACGAACCAGTTAAAAGGATGAATCTGAATACTTTTGT
      1051   ---------+---------+---------+---------+---------+  1100
  a            Q  S  L  L  N  E  P  V  K  R  M  N  L  N  T  F  V  -
  b                                                                -
  c                                                                -
      1051   ---------+---------+---------+---------+---------+  1100
  d                                                                -
  e                                                                -
  f                                                                -

CGTTGAAGAAACAGGTGAAGGTACCAATGCAGAAGCTTTAGACAGGCTGG
      1101   ---------+---------+---------+---------+---------+  1150
  a             V  E  E  T  G  E  G  T  N  A  E  A  L  D  R  L  A  -
  b                                                                -
  c                                                                -
      1101   ---------+---------+---------+---------+---------+  1150
  d                                                                -
  e                                                                -
  f                                                                -

CTCAGATTCTTTATGAAGAAAAGATTACTCGTGGTCTCGGAAAGATATCT
      1151   ---------+---------+---------+---------+---------+  1200
  a              Q  I  L  Y  E  E  K  I  T  R  G  L  G  K  I  S    -
  b                                                                -
  c                                                                -
      1151   ---------+---------+---------+---------+---------+  1200
  d                                                                -
  e                                                                -
  f                                                                -

TTGGAAGTGGATAACATTGATCCATATACTGAACGTGTTAGGAAACTGCT
      1201   ---------+---------+---------+---------+---------+  1250
  a            L  E  V  D  N  I  D  P  Y  T  E  R  V  R  K  L  L   -
  b                                                                -
  c                                                                -
      1201   ---------+---------+---------+---------+---------+  1250
  d                                                                -
  e                                                                -
  f                                                                -

ATTCTGATACGAATTGAAGTTGTTTCCTCCTTGCCATATAGCCTCACTTT
      1251   ---------+---------+---------+---------+---------+  1300
  a            F  *
  b                                                                -
  c                                                                -
      1251   ---------+---------+---------+---------+---------+  1300
  d                                                                -
  e                                                                -
  f                                                                -
              GTTTGGCAATAAATAAATAAATAAATGTAATCGTTTGGTTTGATGTCCTT
      1301   ---------+---------+---------+---------+---------+  1350
  a                                                                -
```

Figure 1E

```
b                                                                                     -
c                                                                                     -
   1301 ---------+---------+---------+---------+---------+---------+ 1350
d                                                                                     -
e                                                                                     -
f                                                                                     -
        GACTTTGTCATATATGCTGGCTCTATAAGAAGCACCAGCAGATAAATAAA
   1351 ---------+---------+---------+---------+---------+---------+ 1400
a                                                                                     -
b                                                                                     -
c                                                                                     -
   1351 ---------+---------+---------+---------+---------+---------+ 1400
d                                                                                     -
e                                                                                     -
f                                                                                     -
        GGTTAATGTTTGAGGTATWAARWAAAAAAAAAAAAAAAAAAAAAAAAAAA
   1401 ---------+---------+---------+---------+---------+---------+ 1450
a                                                                                     -
b                                                                                     -
c                                                                                     -
   1401 ---------+---------+---------+---------+---------+---------+ 1450
d                                                                                     -
e                                                                                     -
f                                                                                     -
        AAAAAAAAAAAAAAACTCGA
   1451 ---------+--------- 1469
a                                       -
b                                       -
c                                       -
   1451 ---------+--------- 1469
d                                       -
e                                       -
f                                       -
```

Figure 1F

With 1 enzymes: HPAI

```
      ATGAAGTCCAAGATGGCCATGCTCCTCCTCCTCTTCTGCGTGCTCTCCAA
   1  ---------+---------+---------+---------+---------+  50
a      M  K  S  K  M  A  M  L  L  L  L  F  C  V  L  S  N   -

CCAGCTCGTGGCCGCGTTCTCCACCCAGGCCAAGGCCTCCAAGGACGGCA
  51  ---------+---------+---------+---------+---------+  100
a       Q  L  V  A  A  F  S  T  Q  A  K  A  S  K  D  G  N  -

ACCTCGTGACCGTGCTCGCCATCGACGGCGGCGGCATCCGCGGCATCATC
 101  ---------+---------+---------+---------+---------+  150
a        L  V  T  V  L  A  I  D  G  G  G  I  R  G  I  I    -

CCGGGCGTGATCCTCAAGCAGCTCGAGGCGACCCTCCAGAGGTGGGACTC
 151  ---------+---------+---------+---------+---------+  200
a      P  G  V  I  L  K  Q  L  E  A  T  L  Q  R  W  D  S   -

CAGCGCCAGGCTCGCGGAGTACTTCGACGTGGTGGCCGGCACCTCCACCG
 201  ---------+---------+---------+---------+---------+  250
a       S  A  R  L  A  E  Y  F  D  V  V  A  G  T  S  T  G  -

GCGGCATCATCACCGCCATCCTCACCGCCCCGGACCCGCAGAACAAGGAC
 251  ---------+---------+---------+---------+---------+  300
a        G  I  I  T  A  I  L  T  A  P  D  P  Q  N  K  D    -

CGCCCGCTCTACGCCGCCGAGGAGATCATCGACTTCTACATCGAGCACGG
 301  ---------+---------+---------+---------+---------+  350
a      R  P  L  Y  A  A  E  E  I  I  D  F  Y  I  E  H  G   -

CCCCGTCCATCTTCAACAAGTCCACCGCCTGCTCCCTCCCGGGCATCTTCT
 351  ---------+---------+---------+---------+---------+  400
a       P  S  I  F  N  K  S  T  A  C  S  L  P  G  I  F  C  -

GCCCGAAGTACGACGGCAAGTACCTCCAGGAGATCATCTCCCAGAAGCTC
 401  ---------+---------+---------+---------+---------+  450
a        P  K  Y  D  G  K  Y  L  Q  E  I  I  S  Q  K  L    -

AACGAGACCCTCCTCGACCAGACCACCACCAACGTGGTGATCCCGTCCTT
 451  ---------+---------+---------+---------+---------+  500
a      N  E  T  L  L  D  Q  T  T  T  N  V  V  I  P  S  F   -

CGACATCAAGCTCCTCCGCCCGACCATCTTCTCCACCTTCAAGCTCGAGG
 501  ---------+---------+---------+---------+---------+  550
```

AGGTGCCGGAGCTCAACGTGAAGCTCTCCGACGTGTGCATGGGCACCTCC
   551   ---------+---------+---------+---------+---------+   600
a          V   P   E   L   N   V   K   L   S   D   V   C   M   G   T   S   -

GCCGCCCCGATCGTGTTCCCGCCGTACTACTTCAAGCACGGCGACACCGA
   601   ---------+---------+---------+---------+---------+   650
a        A   A   P   I   V   F   P   P   Y   F   K   H   G   D   T   E   -

GTTCAACCTCGTCGACGGCGCGATCATCGCGGACATCCCAGCCCCGGTGG
   651   ---------+---------+---------+---------+---------+   700
a         F   N   L   V   D   G   A   I   I   A   D   I   P   A   P   V   A   -

CCCTCTCCGAGGTGCTCCAGCAGGAGAAGTACAAGAACAAGGAGATCCTC
   701   ---------+---------+---------+---------+---------+   750
a            L   S   E   V   L   Q   Q   E   K   Y   K   N   K   E   I   L   -

CTCCTGAGCATCGGCACCGGCGTGGTGAAGCCGGGCGAGGGCTACTCCGC
   751   ---------+---------+---------+---------+---------+   800
a        L   L   S   I   G   T   G   V   V   K   P   G   E   G   Y   S   A   -

CAACCGCACCTGGACCATCTTCGACTGGTCCTCCGAGACCCTCATCGGCC
   801   ---------+---------+---------+---------+---------+   850
a          N   R   T   W   T   I   F   D   W   S   S   E   T   L   I   G   L   -

TCATGGGGCACGGCACCCGCGCCATGTCCGACTACTACGTGGGCTCCCAC
   851   ---------+---------+---------+---------+---------+   900
a           M   G   H   G   T   R   A   M   S   D   Y   Y   V   G   S   H   -

TTCAAGGCCCTCCAGCCGCAGAACAACTACCTCCGCATCCAGGAGTACGA
   901   ---------+---------+---------+---------+---------+   950
a         F   K   A   L   Q   P   Q   N   N   Y   L   R   I   Q   E   Y   D   -

CCTCGACCCGGCCCTCGAGTCCATCGACGACGCCTCCACCGAGAACATGG
   951   ---------+---------+---------+---------+---------+  1000
a        L   D   P   A   L   E   S   I   D   D   A   S   T   E   N   M   E   -

AGAACCTCGAGAAGGTGGGCCAGTCCCTCCTCAACGAGCCGGTGAAGCGC
  1001   ---------+---------+---------+---------+---------+  1050
a           N   L   E   K   V   G   Q   S   L   L   N   E   P   V   K   R   -

ATGAACCTCAACACGTTCGTCGTGGAGGAGACCGGCGAGGGGACCAACGC
  1051   ---------+---------+---------+---------+---------+  1100
a        M   N   L   N   T   F   V   V   E   E   T   G   E   G   T   N   A   -

CGAGGCGCTCGACCGCCTCGCCCAGATCCTCTACGAGGAGAAGATCACCC
  1101   ---------+---------+---------+---------+---------+  1150
```

GCGGCCTCGGCAAGATCTCCCTCGAGGTGGACAACATCGACCCGTACACC
   1151  ---------+---------+---------+---------+---------+  1200
a        G   L   G   K   I   S   L   E   V   D   N   I   D   P   Y   T   -

GAGCGCGTGCGCAAGCTCCTCTTCTGA
   1201  ---------+---------+-------   1227
a        E   R   V   R   K   L   L   F   *   -
```

Figure 2C

11511p1.Pep Length: 409
(underline represents putative signal sequence)

```
  1  MKSKMAMLLL LFCVLSNQLV AAFSTQAKAS KDGNLVTVLA IDGGGIRGII

51  PGVILKQLEA TLQRWDSSAR LAEYFDVVAG TSTGGIITAI LTAPDPQNKD

101  RPLYAAEEII DFYIEHGPSI FNKSTACSLP GIFCPKYDGK YLQEIISQKL

151  NETLLDQTTT NVVIPSFDIK LLRPTIFSTF KLEEVPELNV KLSDVCMGTS

201  AAPIVFPPYY FKHGDTEFNL VDGAIIADIP APVALSEVLQ QEKYKNKEIL

251  LLSIGTGVVK PGEGYSANRT WTIFDWSSET LIGLMGHGTR AMSDYYVGSH

301  FKALQPQNNY LRIQEYDLDP ALESIDDAST ENMENLEKVG QSLLNEPVKR

351  MNLNTFVVEE TGEGTNAEAL DRLAQILYEE KITRGLGKIS LEVDNIDPYT

401  ERVRKLLF*
```

Figure 3

PROTEIN HAVING INSECTICIDAL ACTIVITIES AND METHOD OF USE

This application claims the benefit of Provisional Application Ser. No. 60/047,864 filed May 29, 1997.

FIELD OF THE INVENTION

The invention relates to compositions and methods for controlling insect species. Additionally, the invention relates to plants and other organisms which have been genetically transformed with the compositions of the invention.

BACKGROUND OF THE INVENTION

Numerous insect species are serious pests to common agricultural crops such as corn, soybeans, peas, cotton, and similar food and fiber crops. The primary method of controlling such pests has been through the application of synthetic chemical compounds. However, the widespread use of chemical compounds poses many problems with regard to the environment because of the non-selectivity of the compounds and the development of insect resistance to the chemicals.

Other approaches to pest control have been tried including the use of biological organisms which are typically "natural predators" of the species sought to be controlled. Such predators may include other insects, fungi, and bacteria such as *Bacillus thuringiensis*. Alternatively, large colonies of insect pests have been raised in captivity, sterilized and released into the environment in the hope that mating between the sterilized insects and fecund wild insects will decrease the insect population. While these approaches have had some success, they entail considerable expense and present several major difficulties. For example, it is difficult both to apply biological organisms to large areas and to cause such living organisms to remain in the treated area or on the treated plant species for an extended time. Predator insects can migrate and fungi or bacteria can be washed off of a plant or removed from a treated area by rain. Consequently, while the use of such biological controls has desirable characteristics and has met with some success, in practice these methods seem severely limited.

Advances in biotechnology in the last two decades have presented new opportunities for pest control through genetic engineering. In particular, advances in plant genetics coupled with the identification of insect growth factors and naturally-occurring plant defensive compounds or agents offer the opportunity to create transgenic crop plants capable of producing such defensive agents and thereby protect the plants against insect attack.

Transgenic plants that are resistant to specific insect pests have been produced using genes encoding *Bacillus thuringiensis* (Bt) endotoxins or plant protease inhibitors (PIs). Transgenic plants containing Bt endotoxin genes have been shown to be effective for control of some insects. Effective plant protection using transgenically inserted PI genetic material has not yet been demonstrated in the field. While cultivars expressing Bt genes may presently exhibit resistance to some insect pests, resistance based on the expression of a single gene might eventually be lost due to the evolution of Bt resistance in the insects. Thus, the search for additional genes which can be inserted into plants to provide protection from insect pests is needed.

Scientists have identified some specific plant components or compounds which act as defensive agents to protect a plant from attack by insect pests and pathogens. While such components are usually present at only low levels in various plant tissues, some of them are also capable of being induced to higher levels upon attack by an insect pest or a pathogen. Examples of such defensive compounds include alkaloids, terpenes, and various proteins such as enzymes, enzyme inhibitors, and lectins. Of particular interest are plant-derived compounds which can block or alter normal biomolecular activity and thus inhibit insect growth or kill the insect.

The corn rootworm (CRW) complex in the United States consists of three species, *Diabrotica barberi* Smith and Lawrence (Northern), *D. undecimpunctata howardi* Barber (Southern) and *D. virgifera virgifera* LeConte (Western). The western and northern species contribute the most to the economic damage to maize. The economic damage and control costs are estimated to exceed one billion dollars a year. As noted above, the major concerns of pesticide use in controlling CRW damage are its negative effect on the environment and the development of resistance by the insect. Crop rotation is becoming less effective as a CRW control method due to extended diapause in the northern CRW and the development of modified egg laying behavior in western CRW. The generation of transgenic plants with resistance to CRW could have a major economic impact. Unfortunately there are relatively few, if any, genes available that can control CRW in transgenic plants. Thus, there is a need for additional insecticidal principles, particularly those active against CRW.

SUMMARY OF THE INVENTION

Compositions and methods for the control of insects and other pests are provided. The compositions comprise proteins having pesticidal activities which can be isolated from plants of the genus Pentaclethra. Purified protein, as well as amino acid and DNA sequence information is provided for proteins having rootworm activity. The DNA sequences encoding the pesticidal proteins can be used to transform plants, bacteria, fungi, yeasts, and other organisms for the control of pests.

The compositions and methods of the invention may be used in a variety of systems for controlling plant and non-plant pests.

BRIEF DESCRIPTION OF THE DRAWINGS

FIG. 1 provides the amino acid and nucleotide sequence of the cDNA sequence of the corn rootworm active principle, Pentin-1, from Pentaclethra SEQ ID NOS:1 and 2.

FIG. 2 provides the amino acid and nucleotide sequence of the CDNA sequence of Pentin-1, optimized for enhanced expression SEQ ID NOS:3 and 4.

FIG. 3 provides the amino acid sequence of the Pentin-1 protein with the underlined portion representing the putative signal sequence. The AFS residues immediately following the signal sequence are the first three residues of the mature protein. The ASK residues beginning five residues from the AFS start of the mature protein designates the region of apparent mature amino terminus of pentin-1 expressed as full length protein and proteolyzed in maize roots.

DETAILED DESCRIPTION OF THE INVENTION

Figure 4:
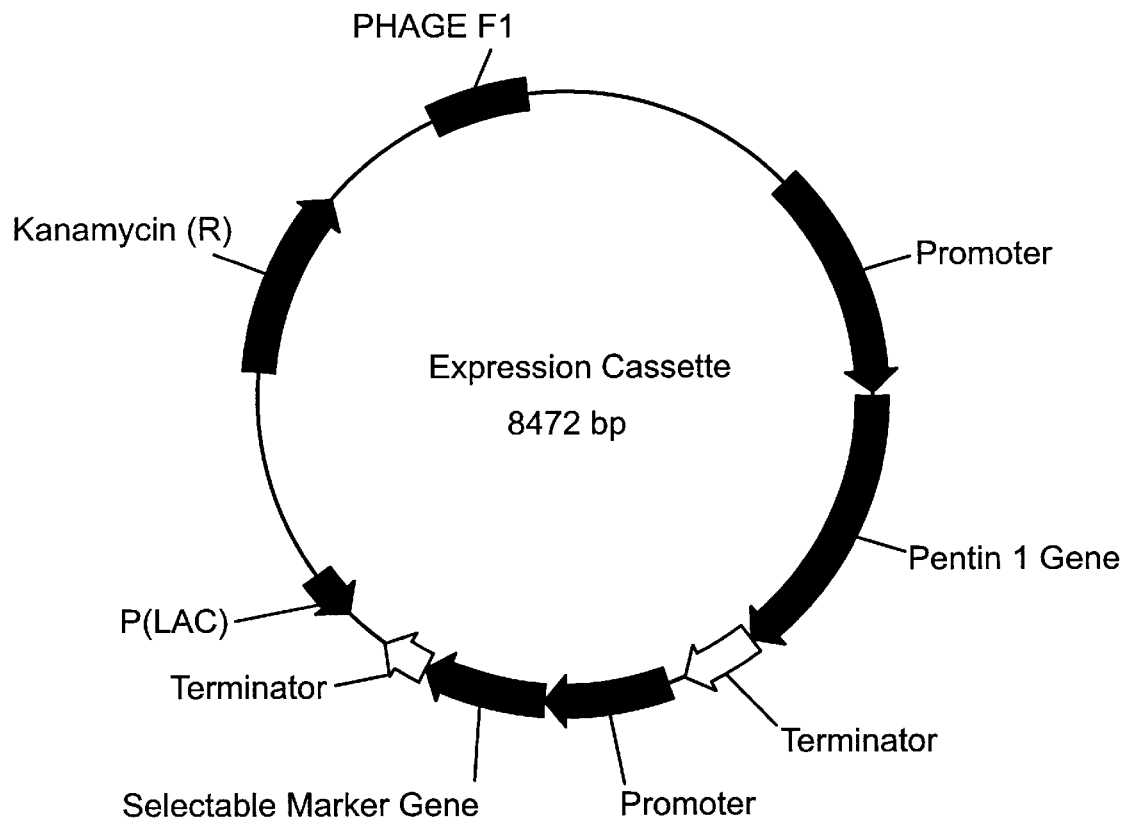
FIG. 4 provides the expression cassette for expression of Pentin-1 sequences.

Compositions and methods for controlling pests, particularly plant pests, are provided. In particular, novel pesticidal proteins are provided. The proteins are purified from members of the family Leguminosae, particularly the Leguminous genus Pentaclethra, more particularly the species *P. macrophylla* and *P. macroloba*.

In accordance with the invention, the pesticidal proteins produced by members of the genus Pentaclethra can be isolated by methods known in the art. Methods for protein isolation include conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. See for example *Current Protocols in Molecular Biology*, Vols. 1 and 2, Ausubel et al. (eds.), John Wiley & Sons, NY (1988), herein incorporated by reference.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) *J. Biol. Chem.* 257:9751–9758; Liu et al. (1983) *Int. J. Pept. Protein Res.* 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

In the same manner, antibodies raised against partially purified or purified peptides can be used to determine the spatial and temporal distribution of the protein of interest. Thus, the tissue where the protein is most abundant, and possibly more highly expressed can be determined and expression libraries constructed. Methods for antibody production are known in the art. See, for example *Antibodies, A Laboratory Manual*, Harlow and Lane (eds.), Cold Spring Harbor Laboratory Press, Cold Spring Harbor, N.Y. (1988), and the references cited therein. See also, Radka et al. (1983) *J. Immunol.* 128:2804; and Radka et al. (1984) *Immunogenetics* 19:63. Such antibodies can be used to isolate proteins with similar binding domains and the proteins tested for activity against insect pests of interest.

It is recognized that any combination of methods may be utilized to purify proteins having pesticidal properties. As an isolation protocol is being determined, the pesticidal activity can be tested for each fraction of material obtained after each purification step.

Such purification protocols will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

From fragments of the protein, the entire nucleotide sequence encoding the protein can be determined by PCR experiments. Likewise, fragments obtained from PCR experiments can be used to isolate cDNA sequences from expression libraries. See, for example, Molecular Cloning, A Laboratory Manual, Second Edition, Vols. 1–3, Sambrook el al. (eds.) Cold Spring Harbor Laboratory Press, Cold Spring Harbor, N.Y. (1989), and the references cited therein.

In this manner, proteins and the nucleotide sequences encoding such proteins can be isolated which are inhibitory or toxic to particular insect species. Such proteins and nucleotide sequences of the invention can be utilized to protect plants from pests, including insects, fungi, bacteria, nematodes, viruses or viroids, and the like, particularly insect pests. In particular, proteins and nucleotide sequences which are inhibitory or toxic to insects of the order Coleoptera can be obtained.

Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera. Insect pests of the invention for the major crops include:

Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica barberi*, northern corn rootworm; *Diabrotica undecimpunctata howardi*, spotted cucumber beetle, Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus*, chinch bug; *Melanoplus femurrubrum*, redlegged grasshopper; *Melanoplus sanguinipes*, migratory grasshopper; *Delia platura*, seedcorn maggot; *Agromyza parvicornis*, corn blotch leafminer; *Anaphothrips obscrurus*, grass thrips; *Solenopsis milesta*, thief ant; *Tetranychus urticae*, twospotted spider mite; *Busseola fusca*, African Maize Stem Borer (AMB); *Sesamia calamistis*, African Pink Borer (APB); *Eldana sacchharina*, African Sugarcane Borer (ASB); *Chilo partellus*, Sorghum Stem Borer (SSB); *Ostrinia furnacalis*, Oriental Corn Borer (OCB); *Sesamia nonagrioides*, Corn borer in Europe/N. Africa; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Agrotis subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus*, chinch bug; *Contarinia sorghicola*, sorghum midge; *Tetranychus cinnabarinus*, carmine spider mite; *Tetranychus urticae*, twospotted spider mite; *Schizaphis graminum*, Greenbug (aphid); Wheat: *Pseudaletia unipunctata*, army worm; *Spodoptera frugiperda*, fall armyworm; *Elasmopalpus lignosellus*, lesser cornstalk borer; *Agrotis orthogonia*, plae western cutworm; *Oulema melanopus*, cereal leaf beetle; *Hypera punctata*, clover leaf weevil; *Diabrotica undecimpunctata howardi*, spotted cucumber beetle; Russian wheat aphid; *Schizaphis graminum*, greenbug; *Sitobion avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Eriophyes tulipae*, wheat curl mite; Sunflower: *Suleima helianthana*, sunflower bud moth; *Homeosoma ellectellum*, sunflower head moth; *Zygoramma exclamationis*, sunflower beetle; *Bothyrus gibbosus*, carrot beetle; *Neolasioptera murtfeldtiana*, sunflower seed midge; *Cochylis hospes*, banded sunflower moth; *Rachiplusia nu*, agentina looper; *Smicronyx fulvus*, red sunflower seed weevil; *Cylindrocopturus adspersus*, spotted sunflower stem weevil; Cotton: *Heliothis virescens*, tobacco budworm; *Helicoverpa zea*, bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhoper; *Blissus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton boll worm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Delia platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; Flea beetle, *Phyllotreta* spp.; Bertha Armyworm; *Mamestra configurata*; Diamondback Moth; *Plutella xylostella*; Alfalfa: alfalfa looper, *Autographa californica*; alfalfa snout beetle, *Otiorhynchus ligusticii*; alfalfa caterpillar, *Colias eurytheme*; alfalfa blotch leafrunner, *Agronyza frontella*; Egyptian alfalfa weevil, *Hypera brunneipeonis*; meadow spittlebug, *Philaerius spumarius*; spotted alfalfa aphid, *Theriophis meculata*; clover leaf weevil, *Hypera punctala*; pea aphid, *Acyrthosiphon pisum*; blue alfalfa aphid, *Acyrthosiphor kondoi*; green cloverworm, *Plathypena scabia*; clover root curculio, *Sitona hispidulus*; alfalfa seed chalcid, *Brachophagus roddi*; tarnished plantbug, *Lygus lineolaris*; Say stink bug, *Chlorochroa sayi*; velvetbean caterpillar, *Anticarsia friegiperda*, alfalfa weevil, *Hypera postica*; fall armyworm, *Spodoptera*; potato leafhopper, *Empoasca fabae*; soybean looper, *Psuedolusia includens*; Three cornered alfalfa hopper, *Spissistilus festinus*; See, for example, Manya B. Stoetzel (1989) *Common Names of Insects & Related Organisms, Entomological Society of America*, herein incorporated by reference.

The nucleotide sequences of the invention can be used to isolate other homologous sequences in other plant species, particularly other Leguminous species. Methods are readily available in the art for the hybridization of nucleic acid sequences. Coding sequences from other plants may be isolated according to well known techniques based on their sequence homology to the coding sequences set forth herein. In these techniques all or part of the known coding sequence is used as a probe which selectively hybridizes to other pesticidal coding sequences present in a population of cloned genomic DNA fragments or cDNA fragments (i.e. genomic or cDNA libraries) from a chosen organism.

For example, the entire Pentin-1 sequence or portions thereof may be used as probes capable of specifically hybridizing to corresponding coding sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify Pentin-1 coding sequences from a chosen organism by the well-known process of polymerase chain reaction (PCR). This technique may be used to isolate additional coding sequences from a desired organism or as a diagnostic assay to determine the presence of Pentin-1 coding sequences in an organism.

Such techniques include hybridization screening of plated DNA libraries (either plaques or colonies; see, e.g. Sambrook et al., *Molecular Cloning*, eds., Cold Spring Harbor Laboratory Press (1989)) and amplification by PCR using oligonucleotide primers corresponding to sequence domains conserved among the amino acid sequences (see, e.g. Innis et al., *PCR Protocols, a Guide to Methods and Applications*, eds., Academic Press (1990)).

For example, hybridization of such sequences may be carried out under conditions of reduced stringency, medium stringency or even stringent conditions (e.g., conditions represented by a wash stringency of 35–40% formamide with 5× Denhardt's solution, 0.5% SDS and 1× SSPE at 37° C.; conditions represented by a wash stringency of 40–45% formamide with 5× Denhardt's solution, 0.5% SDS, and 1× SSPE at 42° C.; and conditions represented by a wash stringency of 50% formamide with 5× Denhardt's solution, 0.5% SDS and 1× SSPE at 42° C., respectively), to DNA encoding the insecticidal genes disclosed herein in a standard hybridization assay. See J. Sambrook et al., *Molecular Cloning, A Laboratory Manual* 2d Ed. (1989) Cold Spring Harbor Laboratory.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequencedependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1,000 nucleotides in length, preferably less than about 500 nucleotides in length, typically from about 50 to about 300 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30 for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50° C. to 55° C. Exemplary moderate stringency conditions include hybridization in 40 to 45% formamide, 1 M NaCl, 1% SDS at 37° C., and a wash in 0.5× to 1× SSC at 55° C to 60° C. Exemplary high stringency conditions include hybridization in 50% formamide, 1 M NaCl, 1% SDS at 37° C., and a wash in 0.1× SSC at 60° C. to 65° C.

Specificity is typically the function of post-hybridization washes, the critical factors being the ionic strength and temperature of the final wash solution. For DNA—DNA hybrids, the Tm can be approximated from the equation of Meinkoth and Wahl, *Anal. Biochem.* 138:267–284 (1984): Tm=81.5C+16.6 (log M)+0.41 (%GC)−0.61 (% form)−500/L; where M is the molarity of monovalent cations, %GC is the percentage of guanosine and cytosine nucleotides in the DNA, % form is the percentage of formamide in guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with ≧90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8 or 9 or 10° C. lower than the thermal melting point (Tm); low stringency conditions can utilize a hybridization and/or wash at 11, 12, 13, 14, 15, or 20° C. lower than the thermal melting point (Tm) Using the equation, hybridization and wash compositions, and desired Tm those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology— Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

In general, sequences which code for Pentin-1 and other insecticidal proteins of the invention and hybridize to the gene disclosed herein will be at least about 50% homologous, about 70% homologous, up to about 85% homologous or more up to about 90% to about 95% homologous with the disclosed sequence. That is, the sequence similarity of sequences may range, sharing at least about 50%, about 70%, and about 85% up to about 90% to 95% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 . (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Groups (GCG), 575 Science Drive, Madison, Wis., USA; the CLUSTAL program is well described by Higgins and Sharp, *Gene* 73:237–244 (1988); Higgins and Sharp, *CABIOS* 5:151–153 (1989); Corpet et al., *Nucleic Acids Research* 16:10881–90 (1988); Huang, et al., *Computer Applications in the Biosciences* 8:155–65 (1992), and Pearson, et al., *Methods in Molecular Biology* 24:307–331 (1994). The BLAST family of programs which can be used for database similarity searches includes: BLASTN for nucleotide query sequences against nucleotide sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

As those of ordinary skill in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.* 17:149–163 (1993) and XNU (Claverie and States, *Comput. Chem.,* 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.* 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical as if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e)(ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

It is recognized that the pesticidal proteins may be oligomeric and will vary in molecular weight, number of promoters, component peptides, activity against particular pests, and in other characteristics. However, by the methods set forth herein, proteins active against a variety of pests may be isolated and characterized. Of particular interest are proteins which are active against corn rootworm (CRW). Thus, the purified or partially purified proteins of the invention are tested for insecticidal activity against corn rootworm, including *Diabrotica barberi* (Northern), *D. undecimpunctata howardi* (Southern), and *D. virgifera vergifera* (Western). In this manner, one protein designated Pentin-1 has been isolated which has insecticidal activity to corn rootworm. Pentin-1 is a glycosylated protein of approximately 45 to about 50 kdal. The amino acid and nucleotide sequence of the Pentin-1 protein is given in FIG. 1 and SEQ ID NOS: 1 and 2.

The highest concentration of Pentin-1 in the plant appears to be in mature seeds. The protein is heat stable and has an LC50 of approximately 10 µg/ml of diet against corn rootworm.

The Pentin-1 and other proteins of the invention may be altered in various ways including amino acid substitutions, deletions, truncations, and insertions. Methods for such manipulations are generally known in the art. For example, amino acid sequence variants of the pesticidal proteins can be prepared by mutations in the DNA. Methods for mutagenesis and nucleotide sequence alterations are well known in the art. See, for example, Kunkel, T. (1985) *Proc.*

Natl. Acad. Sci. USA 82:488–492; Kunkel et al. (1987) Methods in Enzymol. 154:367–382; U.S. Pat. No. 4,873,192; Walker and Gaastra (eds.) *Techniques in Molecular Biology*, MacMillan Publishing Company, NY (1983) and the references cited therein. Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component promoters, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by insect toxicity assay.

The nucleotide sequences can be used in DNA shuffling protocols. DNA shuffling is a process for recursive recombination and mutation, performed by random fragmentation of a pool of related genes, followed by reassembly of the fragments by primerless PCR. See, for example, Stemmer, W. P. C. (1994) *Proc. Natl. Acad. Sci. USA* 91:10747–10751; Stemmer, W. P. C. (1994) *Nature* 370:389–391; Zhang et al. (1997) *Proc. Natl. Acad. Sci. USA* 94:4504–4509; and PCT Publication No. 96/19256. An advantage of DNA shuffling of a rational design is that shuffling can optimize the function of genes without first determining which gene product is rate limiting. The present invention provides methods for sequenced shuffling utilizing polypeptides of the invention, and compositions resulting therefrom.

Generally, sequenced shuffling provides a means for generating libraries of polynucleotides having a desired characteristic which can be selected or screened for. Libraries of recombinant polypeptides are generated from a population of related sequence polypeptides that comprise sequenced regions which have substantial sequence identity and can be homologously recombined in vitro or in vivo.

The population of sequenced-recombined polynucleotides comprises a subpopulation of polynucleotides which possess desired or advantageous characteristics and can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin confirmation, translation, or other expression property of a gene or transgene, a replicative element, a protein-binding element, or the like, such as any feature which confers a selectable or detectable property. In some embodiments, the selected characteristic will be an increased Km and/or Kcat over the wild-type protein as provided herein. In other embodiments, a protein or polynucleotide generated from sequenced shuffling will have a ligand binding affinity greater than the non-shuffled wild-type polynucleotide. The increase in such properties can be at least 110%, 120%, 130%, 140% or at least 150% of the wild-type value.

Pentin-1 is a member of a broader gene family of esterases, and more specifically lipid acyl hydrolases as determined by sequence similarity. Gene shuffling is a method that can improve or alter a biological activity of a given gene product. Gene shuffling, in conjunction with a selection strategy, can be used to improve properties such as substrate specificity, solubility, temperature and pH optima of a protein or enzyme by directed molecular evolution. In the case of Pentin-1 toxicity toward insects as determined by the lethal concentrations is a most relevant parameter.

Gene shuffling can be applied to a single gene which introduces mutations within that gene at a given frequency. Combinations of synergistic mutations can then be selected by subsequent generations of gene shuffling from the primary mutant population. This approach can be applied to Pentin-1.

Alternatively, different members of gene families that are already encoded by divergent but related sequences can be used for gene shuffling. These could include but not be limited to Pentin-1, from Pentaclethra and an expressed sequence tag from maize identified as 5C9 that encodes a cDNA that is about 57% identical to Pentin-1 at the nucleotide level. See copending patent application Ser. No. 08/449,986 filed May 25, 1995, herein incorporated by reference. Concomitantly mutations will also be introduced by gene shuffling further contributing to the genetic diversity. Then synergistic combinations of fusions between the members of the gene family and newly introduced mutations can be selected by directed molecular evolution strategies.

Lipid acyl hydrolases comprise a diverse multigene family that is conserved across many plant species. The enzymes exhibit hydrolyzing activity for many glyco- and phospholipids. Substrates include monogalactosyldiacylglycerol, acylsterylgucoside, phosphatidylcholine, lysophosphatidylcholine, phosphatidylethanolamine, lysophosphatidylethanolamine, phosphatidylinositol, as well as many other lipid substrates. Similarly membrane composition of various insects as well as plants can vary from species to species and can be affected by diet or growth conditions. Consequently, the activity of a given lipid acyl hydrolase for a given substrate could affect both specificity and potency. Altered substrate specificity could be one parameter for selection of products of gene shuffling.

Solubility and protein stability could also be selected from shuffled gene products. Insecticidal proteins are active in the harsh environment of the insect gut lumen. Their proteins are digested by proteases, and affected by reducing or oxidizing conditions that vary according to the insect species tested. The solubility and stability of lipid acyl hydrolases both in the transgenic plant and in the insect gut lumen could affect biological activity and could be altered through gene shuffling strategies.

Conditions for the enzyme reaction such as pH and temperature optima may also affect the insecticidal activity of the Pentin-1. The gut pH of corn rootworm is 5.5–6.0. Selection of shuffled Pentin-1 gene products for enzymatic activity toward lipid substrates in this pH range is another parameter that could affect toxicity.

Thus, the pentin sequence of the present invention can be utilized in gene shuffling experiments with other lipid hydrolases such as patatins, and in particular with 5C9.

The proteins or other component polypeptides described herein may be used alone or in combination with other proteins or agents to control different insect pests. Other insecticidal proteins include those from Bacillus, including δ-endotoxins and vegetative insecticidal proteins, as well as protease inhibitors (both serine and cysteine types), lectins, cc-amylases, peroxidases, cholesterol oxidase, and the like.

In one embodiment, expression of the proteins of the invention in a transgenic plant is accompanied by the expression of one or more *Bacillus thuringiensis* (Bt) δ-endotoxins. This co-expression of more than one insecticidal principle in the same transgenic plant can be achieved by genetically engineering a plant to contain and express all the genes necessary. Alternatively, a plant, Parent 1, can be genetically engineered for the expression of proteins of the invention. A second plant, Parent 2, can be genetically engineered for the expression of other principles, such as a Bt δ-endotoxin. By crossing Parent 1 with Parent 2, progeny plants can be obtained which express all the genes present in both Parents 1 and 2.

The present invention also encompasses nucleotide sequences from organisms other than Pentaclethra, where the proteins cross-react with antibodies raised against the proteins of the invention or where the nucleotide sequences are isolatable by hybridization with the nucleotide sequences of the invention. The proteins isolated or those encoded by such nucleotide sequences can be tested for pesticidal activity. The isolated proteins can be assayed for pesticidal activity by the methods disclosed herein or others well-known in the art.

In another embodiment, the proteins of the invention can be used in combination with seed coatings available in the art. In this manner, transformed seed are coated with applications of available insecticide sprays or powders. Such insecticides are known in the art. See, for example, U.S. Pat. Nos. 5,696,144; 5,695,763; 5,420,318; 5,405,612; 4,596,206; 4,356,934; 4,886,541; etc., herein incorporated by reference.

Once the nucleotide sequences encoding the pesticidal proteins of the invention have been isolated, they can be manipulated and used to express the protein in a variety of hosts including other organisms, including microorganisms and plants.

The proteins of the invention may be used for protecting agricultural crops and products from pests by introduction via a suitable vector into a microbial host, and said host applied to the environment or plants. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

The proteins of the invention can be used in expression cassettes for expression in any host of interest. Such expression cassettes will comprise a transcriptional initiation region linked to the gene encoding the pesticidal gene of interest. Such an expression cassette is provided with a plurality of restriction sites for insertion of the gene of interest to be under the transcriptional regulation of the regulatory regions. The expression cassette may additionally contain selectable marker genes suitable for the particular host organism.

The transcriptional initiation region, the promoter, may be native or analogous or foreign or heterologous to the host. Additionally, the promoter may be the natural sequence or alternatively a synthetic sequence. By foreign is intended that the transcriptional initiation region is not found in the wild-type host into which the transcriptional initiation region is introduced. As used herein a chimeric gene comprises a coding sequence operably linked to transcription initiation region which is heterologous to the coding sequence. While any promoter or promoter element capable of driving expression of a coding sequence can be utilized, of particular interest for expression in plants are root promoters (Bevan et al. (1993) in *Gene Conservation and Exploitation. Proceedings of The 20th Stadler Genetics Symposium*, Gustafson et al. (eds.), Plenum Press, New York pp. 109–129; Brears et al. (1991) *Plant J.* 1:235–244; Lorenz et al. (1993) *Plant J.* 4:545–554; U.S. Pat. Nos. 5,459,252; 5,608,149; 5,599,670); pith (U.S. Pat. Nos. 5,466,785; 5,451,514; 5,391,725); or other tissue specific and constitutive promoters (See, for example, U.S. Pat. Nos. 5,608,149; 5,608,144; 5,604,121; 5,569,597; 5,466,785; 5,399,680; 5,268,463; 5,608,142), herein incorporated by reference.

The transcriptional cassette will include in 5'–3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639.

The nucleotide sequences encoding the proteins or polypeptides of the invention are particularly useful in the genetic manipulation of plants. In this manner, the genes of the invention are provided in expression cassettes for expression in the plant of interest. The cassette will include 5' and 3' regulatory sequences operably linked to the gene of interest. The cassette may additionally contain at least one additional gene to be cotransformed or linked and transformed into the organism. Alternatively, the gene(s) of interest can be provided on another expression cassette. Where appropriate, the gene(s) may be optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436,391, and Murray et al. (1989) *Nucleic Acids Res.* 17:477–498, herein incorporated by reference.

Depending upon where the DNA sequence of interest is to be expressed, it may be desirable to synthesize the sequence with plant preferred codons, or alternatively with chloroplast preferred codons. The plant preferred codons may be determined from the codons of highest frequency in the proteins expressed in the largest amount in the particular plant species of interest. See, EPA 0359472; EPA 0385962; WO 91/16432; Perlak et al. (1991) *Proc. Natl. Acad. Sci. USA* 88:3324–3328; and Murray et al. (1989) *Nucleic Acids Research* 17:477–498. In this manner, the nucleotide sequences can be optimized for expression in any plant. It is recognized that all or any part of the gene sequence may be optimized or synthetic. That is, synthetic or partially optimized sequences may also be used.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA,* 86:6126–6130); potyvirus leaders, for example, TEV leader (Tobacco Etch Virus) (Allison et al. (1986)); MDMV leader (Maize Dwarf Mosaic Virus) *Virology,* 154:9–20); and human immunoglobulin heavy-chain binding protein (BiP), (Macejak, D. G., and Sarnow, P. (1991) *Nature,* 353:90–94; untranslated leader from the coat protein mRNA of alfalfa mosaic virus (AMV RNA 4), (Jobling, S. A., and Gehrke, L., (1987) *Nature,* 325:622–625); tobacco mosaic virus leader (TMV), (Gallie, D. R. et al. (1989) *Molecular Biology of RNA,* pages 237–256); and maize chlorotic mottle virus leader (MCMV) (Lommel, S. A. et al. (1991) *Virology,* 81:382–385). See also, Della-Cioppa et al. (1987) *Plant Physiology,* 84:965–968. Other methods known to enhance translation can also be utilized, for example, introns, and the like.

The genes of the present invention can be targeted to the chloroplast or amyloplast for expression. In this manner, where the gene of interest is not directly inserted into the chloroplast or amyloplast, the expression cassette will additionally contain a gene encoding a transit peptide to direct the gene of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and Shah et al. (1986) *Science* 233:478–481.

The construct may also include any other necessary regulators such as nuclear localization signals (Kalderon et al. (1984) *Cell* 39:499–509; and Lassner et al. (1991) *Plant Molecular Biology* 17:229–234); plant translational consensus sequences (Joshi, C. P. (1987) *Nucleic Acids Research* 15:6643–6653), introns (Luehrsen and Walbot (1991) *Mol. Gen. Genet.* 225:81–93) and the like, operably linked to the nucleotide sequence of interest.

It is recognized that the protein can be expressed comprising the native signal sequence. See FIG. 3. Alternatively, other signal sequences in the art, for example the barley alpha amylase signal sequence, may be utilized.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g. transitions and transversions, may be involved.

The compositions of the present invention can be used to transform any plant. In this manner, genetically modified plants, plant cells, plant tissue, seed, and the like can be obtained. Transformation protocols may vary depending on the type of plant or plant cell, i.e. monocot or dicot, targeted for transformation. Suitable methods of transforming plant cells include microinjection (Crossway et al. (1986) *Biotechniques* 4:320–334), electroporation (Riggs et al. (1986) *Proc. Natl. Acad. Sci. USA,* 83:5602–5606, Agrobacterium mediated transformation (Hinchee et al. (1988) *Biotechnology,* 6:915–921), direct gene transfer (Paszkowski et al. (1984) *EMBO J.,* 3:2717–2722), and ballistic particle acceleration (see, for example, Sanford et al., U.S. Pat. No. 4,945,050; and, McCabe et al. (1988) *Biotechnology,* 6:923–926). Also see, Weissinger et al. (1988) *Annual Rev. Genet.,* 22:421–477; Sanford et al. (1987) *Particulate Science and Technology,* 5:27–37 (onion); Christou et al. (1988) *Plant Physiol.* 87:671–674 (soybean); McCabe et al. (1988) *Bio/Technology,* 6:923–926 (soybean); Datta et al. (1990) *Biotechnology,* 8:736–740 (rice); Klein et al. (1988) *Proc. Natl. Acad. Sci. USA,* 85:4305–4309 (maize); Klein et al. (1988) *Biotechnology,* 6:559–563 (maize); Klein et al. (1988) *Plant Physiol.,* 91:440–444 (maize); Fromm et al. (1990) *Biotechnology,* 8:833–839; Tomes et al. "Direct DNA transfer into intact plant cells via microprojectile bombardment," In: Gamborg and Phillips (eds) Plant Cell, Tissue and Organ Culture: Fundamental Methods, Springer-Verlag, Berlin, 1995 (maize); Hooydaas-Van Slogteren & Hooykaas (1984) *Nature* (London), 311:763–764; Bytebier et al. (1987) *Proc. Natl. Acad. Sci. USA,* 84:5345–5349 (Liliaceae); De Wet et al. (1985) In *The Experimental Manipulation of Ovule Tissues,* ed. G. P. Chapman et al., pp. 197–209. Longman, N.Y. (pollen); Kaeppler et al. (1990) *Plant Cell Reports,* 9:415–418; and Kaeppler et al. (1992) *Theor. Appl. Genet.,* 84:560–566 (whisker-mediated transformation); D=Halluin et al. (1992) *Plant Cell,* 4:1495–1505 (electroporation); Li et al. (1993) *Plant Cell Reports,* 12:250–255 and Christou and Ford (1995) *Annals of Botany,* 75:407–413 (rice); Osjoda et al. (1996) *Nature Biotechnology,* 14:745–750 (maize via *Agrobacterium tumefaciens*); all of which are herein incorporated by reference.

Where desirable, the plant plastid can be transformed directly. Stable transformation of plastids have been reported in higher plants, see, for example, SVAB et al. (1990) *Proc. Natl. Acad. Sci. USA* 87:8526–8530; SVAB & Maliga (1993) *Proc. Natl. Acad. Sci. USA* 90:913–917; Staub & Maliga (1993) *Embo J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-specific expression of a nuclear-encoded and plastid-directed RNA polymerase. Such a system has been reported in McBride et al. (1994) *Proc. Natl. Acad. Sci. USA* 91:7301–7305.

The cells which have been transformed may be grown into plants in accordance with conventional ways. See, for example, McCormick et al. (1986) *Plant Cell Reports,* 5:81–84. These plants may then be grown, and either pollinated with the same transformed strain or different strains, and the resulting offspring having the desired phenotypic characteristic identified. Two or more generations may be grown to ensure that the subject phenotypic characteristic is stably maintained and inherited and then seeds harvested to ensure the desired phenotype or other property has been achieved.

The proteins will be expressed in the transformed organisms in amounts to be toxic to the insects of interest or inhibitory to insect growth.

The following examples are offered by way of illustration and not by way of limitation.

Although the foregoing invention has been described in some detail by way of illustration and example for purposes of clarity of understanding, it will be obvious that certain changes and modifications may be practiced within the scope of the described invention.

EXPERIMENTAL

Purification of Pentin-1

P. macroloba seeds were collected from the lowland moist forest of Costa Rica and transported to the inventors' laboratories where they were sliced, lyophilized and stored at −20° C. prior to use. Frozen seeds were diced into smaller pieces and homogenized using a Brinkmann homogenizer. In a typical procedure, 10 grams of seed material was homogenized with 1–2 grams of insoluble polyvinylpyrrolidone and 50–100 ml of 10 mM sodium phosphate buffer, pH 7.5. The homogenate was then stirred at 4° C. for 8–10 hours and centrifuged at 5,000 rpm for 15 minutes. The supernatant fluid was carefully decanted and poured through a single layer of Miracloth, and collected so as to avoid the transfer of lipid-like materials in the extract which have separated and solidified on the surface during centrifugation. The pellet was discarded and the collected liquid, which was still somewhat cloudy, was centrifuged a second time at 18,000 rpm in a Sorvall SS-34 rotor, or its equivalent, for 30 minutes. The slightly turbid supernatant liquid, hereafter called the crude extract, was collected and the pellet was discarded. A sample of the crude extract was saved for testing and the remainder was dialyzed using a 3,500 molecular weight cutoff (MWCO) membrane against five changes of 10 mM sodium phosphate buffer, pH 7.5, at 3° C. to 4° C. The ratio of dialysis fluid to extract was at least 20:1. Dialysis was continued for 8–16 hours per buffer exchange. The extract became quite turbid during dialysis as a result of protein precipitation. Therefore, the dialyzed extract was clarified by centrifugation at 18,000 rpm for 30 minutes to remove denatured proteins. The resulting material, after centrifugation, is hereafter called crude dialyzed extract. The crude and crude dialyzed extracts were analyzed for protein composition or content, and were found to contain a substance which was an insecticidally active against corn rootworm (CRW) in biological assays. The insecticide was found to be a protein or proteinaceous substance.

A 100-ml sample of the dialyzed crude extract was heated to about 80° C. using a water bath and held at this temperature for about 5 minutes. The heated extract was then cooled below 25° C. using an ice bath and, after cooling, centrifuged for 15–30 minutes at 18,000 rpm using a Sorval SS-34 rotor. The clear supernatant liquid was removed, saved and designated hereafter as heat-treated extract. The pelleted material was discarded. It was noted that the heat-treated extract sometimes exhibited a tendency to gel. The heat-treated extract was assayed protein for using the Bradford method with BSA as the standard and was found to possess insecticidal activity against CRW in biological assays.

A sample of the heated extract was fractionated and concentrated using ammonium sulfate. The sample was cooled using an ice bath and powdered ammonium sulfate, 0.6 g/ml sample, was slowly added with stirring. Once the ammonium sulfate addition was completed, the sample was maintained at ice bath temperatures for about 30 minutes. The sample was then centrifuged at 4° C. for 20 minutes at 18,000 rpm using a Sorval SS-34 rotor. The supernatant liquid and the pelleted material were separated, and the pelleted material was resolubilized in a minimum amount of 10 mM sodium phosphate buffer, pH 7.5, and dialyzed extensively against 10 mM sodium phosphate buffer, pH 7.5. The supernatant liquid and the resolubilized pelleted material were assayed for protein content by the Bradford method using BSA as the standard and tested for biological activity against CRW. The majority of the Pentin-1 was found in the pelleted material and it was insecticidal against CRW. Alternatively, the volume of the heated extract was reduced by centrifugal concentration using Centricon™ or similar concentrating devices according to the manufacturer's directions.

The proteins were also fractionated by size-exclusion chromatography on either a Pharmacia Sephacryl S-200 column or a Pharmacia Superose 12 column.

Different column sizes were used depending on the amount of protein in the sample which was to be chromatographed. Generally, the volume of sample was no more than 0.5–1% of the column volume. The column were equilibrated with at least two to three column volumes of 10 mM sodium phosphate buffer, pH 7.5, before the sample was applied to the column. The proteins were eluted from the column with 10 mM sodium phosphate buffer, pH 7.5. The fractions were assayed for protein content by the Bradford method using BSA as the standard and were bioassayed using corn rootworm larvae. Crude or dialyzed extracts, heated extracts, fractions resolubilized after ammonium sulfate precipitation, and extracts or fractions concentrated by other methods can be chromatographed by this method. The biologically-active material was eluted just after the void volume, suggesting that the active material is of moderately high molecular weight. This result is consistent with estimates of size obtained using Centricon™ filtration devices with different molecular weight ranges. The latter indicated that the active material has a native molecular weight greater than 100 kDa, the probable result of combining a plurality of subunits of 40–55±5 kDa molecular weight. The purity of the fractions was estimated after molecular weight determination using SDS-PAGE as described below. These fractions were essentially pure with one primary band detected with an estimated subunit molecular weight in the range of 40–55±5 kDa.

Heat-treated samples or samples which had been subjected to size-exclusion chromatography were fractionated by anion exchange chromatography using either a Pharmacia Q Sepharose column or a Pharmacia Resource Q column. Prior to placement of the sample on the column, the column was first washed with 25 mM Tris-HCl or suitable buffer containing 1 M NaCl, and then equilibrated with the same buffer without NaCl. The pH of the buffers used in the chromatography ranged between pH 4 and pH 10. For the purpose of illustrating the methods, chromatography using 25 mM Tris-HCl buffer, pH 9.0, is described herein. Prior to injecting the sample onto the column, the sample was dialyzed using a 3,500 MWCO membrane through 2–3 exchanges of 25 mM Tris-HCl buffer without 1 M NaCl. After placement on the column, the flow-through was collected and the column was washed with 25 mM Tris-HCl, pH 9.0. The wash was also collected. The column was then eluted with a gradient ranging from 25 mM Tris-HCl, pH 9.0, no NaCl to 25 mM Tris-HCl, pH 9.0, 1 M NaCl. All fractions collected were dialyzed with a minimum of two buffer exchanges against 10 mM sodium phosphate, pH 7.5. The flow-through, wash and the salt-eluted fractions were assayed for protein by the Bradford method using BSA as the standard and bioassayed using CRW. Active material was found in the flow-through and in fractions which were eluted between 0.2 and 0.5 M NaCl. To determine whether the capacity of the column was exceeded, resulting in additional materials passing through the column without binding. the active material in the flow-through was reapplied to the column after re-equilibration. Most of the UV 280 nm absorbing material passed through the column. These observations suggested this active material has different properties than the material which bound to the column and was eluted with the increasing increments of NaCl. The other buffers used were also suitable for anion exchange chromatography as known to those familiar with the art. Active material could also be purified by cation-exchange chromatography.

The Pentin-1 material was purified to near homogeneity by size-exclusion chromatography or anion-exchange chromatography. Minor protein bands were removed by high pressure liquid chromatography (HPLC) using a reverse phase column prior to amino acid analysis and determination of the amino acid sequence.

The purity of the samples and the subunit molecular weight were determined by SDS-PAGE using 12% polyacrylamide gels and generally following the method of Laemmli, *Nature* 227:680–685 (1970). Gels were stained with either Coomassie Blue R250 using standard protocols or silver stained (Hammer et al., *Phytochemistry* 28:3019–3026 (1989)). By SDS-PAGE, the subunit molecular weight of the active substance was found to be in the range 40–55,000±5,000 Daltons.

In addition to the procedures described above, other procedures can be used for separating the active substance from a crude seed extract. For example, an extract can be subjected to isoelectric focusing (IEF) using the Rotofor system (Bio-Rad). The Rotofor separates molecules on the basis of their pI or isoelectric point. Every molecule will have a specific charge, either positive or negative, at a specific pH. The Rotofor, using an electrical current, moves molecules through a pH gradient until they reach their pI; i.e., the pH at which they have zero net charge. The molecule stops migrating at its pI because it is no longer affected by the electrical current. The focusing chamber of the Rotofor is separated into twenty smaller chambers by permeable membranes. These twenty samples are removed simultaneously to ensure as little mixing as possible.

Typically, a sample is placed in the focusing medium, a buffered solution (see manufacturer's instructions) which includes 12.5% (w/v) glycerol and 2.5% of pH 3–10 Ampholytes (Bio-Rad). After focusing, the fractions are collected, the pH of each determined and each fraction dialyzed against 1 M NaCl using a 3,500 MWCO membrane to remove the Ampholytes. The samples are then dialyzed against deionized water to remove the NaCl. Each fraction is lyophilized and resuspended in 0.4 ml of 10 mM NaCl. The Rotofor fractions containing active material can be determined by protein assay and bioassay with insect larvae. The Rotofor fractions can then be subjected to further treatment or separation as described above.

Biological Assays

Bioassays were conducted using CRW neonate larvae reared on artificial diets containing Pentin-1 obtained from *P. macroloba* as described herein. The Pentin-1 may be from crude extract or purified as taught herein. Pentin-1 was either topically applied to the diet surface or incorporated into the diet as taught by Czapla and Lang, *J. Econo. Ento.* 83(6):2480–2485 (1990). The culture tray used in the bioassays were divided into treatment groups. One or a plurality of Pentin-1 preparations or fractions from the various separations were screened in each tray; each preparation or fraction being applied to a plurality of cells. Each cell was infested with one or two neonate larvae. A Mylar film with ventilation holes was affixed to the top of each tray to prevent escape and allow air exchange.

For the topical (overlay) assays, a 2% Pentin-1 containing solution was prepared in 0.1 M phosphate buffered saline (PBS), pH=7.8. Seventy-five microliters of Pentin-1 buffer solution were pipetted onto the Stoneville diet medium in each cell. The culture tray was rotated to ensure equal distribution of the Pentin-1 solution on the diet medium. The cells were infected and sealed as described above. The control was 75 $\mu$l of 0.1 M PBS (only) per cell.

For the diet incorporation assays, Stoneville medium was prepared in standard fashion, but with only 90% of the prescribed water. Pentin-1 was added such that the amount in the diet was in the range of 1–5 $\mu$g/g. The control treatment consisted of 0.9 ml PBS buffer added to 8.1 g of medium. The medium was poured into the cells and the cells were then infested and covered as described above. Insect weights (Weight or Avg. Wt.) were determined at Day 7 and are given in the tables.

TABLE A

Effect of Pentin-1 on Southern Corn Rootworm.

| Sample | Concentration ($\mu$g/ml diet) | % Mortality |
|---|---|---|
| Control | — | 0 |
| Crude | 1,000 | 100 |
| Crude | 400 | 15 |
| AS75 | 400 | 60 |
| Size Fraction 17 | 8 | 14 |
| Size Fraction 18 | 8 | 45 |
| Size Fraction 19 | 8 | 29 |

Notes:
AS75 = Ammonium sulfate 75% population

Once Pentin-1 was purified and its insecticidal activity was established, cloning efforts were undertaken. The first step of the process was to determine by western blot analysis the temporal and spatial distribution of Pentin-1 in order to identify the plant or seed tissue or tissues most likely expressing this protein. Since Pentin-1 was not isolated in quantities which allowed for the production of antibodies, the protein was sequenced in order to permit the design of peptides for synthesis. The amino acid sequence data for Pentin-1 is shown below in FIG. 1. Carboxy-terminus and the internal sequence of approximately forty percent of the Pentin-1 peptides was compiled from fifteen peptides purified from LysC and CNBr digestion of purified Pentin-1 protein. The NH2-terminal sequence was not identified during this process.

Antibodies were raised against five of the peptides. The synthetic peptides used to produce antibodies are listed below.

Synthetic Peptide No. 1 (SEQ ID NO:5)

Met Ser Thr Ser Ala Ala Pro Ile Val Phe Pro Pro Tyr Tyr Phe Lys

Note: Corresponds to amino acid numbers 213–228 of FIG. 1.

Synthetic Peptide No. 2 (SEQ ID NO:6)

Ala Leu Gln Pro Gln Asn Asn Tyr Leu Arg Gln Glu Try Asp Leu Asp

Note: Corresponds to amino acid numbers 344–360 of FIG. 1.

Synthetic Peptide No. 3 (SEQ ID NO:7)

Pro Asp Trp Val Val Ile Arg Ser Glu Ser Val Gly Lys

Note: No correspondence to amino acids of FIG. 1.

Synthetic Peptide No. 4 (SEQ ID NO:8)

Lys Ala Phe Val Asn Gly Val Tyr Phe Ile Asn Thr Tyr Asp Ser Ala

Note: No correspondence to amino acids of FIG. 1.

Synthetic Peptide KS (SEQ ID NO:9)

Asn Asn Tyr Leu Arg Ile Gln Glu Tyr Asp Leu Pro Pro Ala Leu

Note: Corresponds to amino acid numbers 349-363 of FIG. 1.

Western dot blots of Pentin-1, each of the synthetic peptides and an experimental protein designated 5C9 were incubated with each of the antibodies. The incubation results indicated that the antibody raised against synthetic peptide KS (antibody anti-KS) and the antibody raised against synthetic peptide 2 (antibody anti-2) recognized Pentin-1. Western blots of *Pentaclethra macroloba* tissue extracts treated with anti-KS antibodies indicated that the greatest recognition was with mature seeds 30–40 mm in diameter or larger. The total RNA was isolated from these seeds.

Genomic DNA was isolated, codon-degenerate oligonucleotides based on peptides were used to PCR amplify genomic fragments. Exon sequence of the resulting clones was used to do RT-PCR with specific oligos, then RT-PCR experiments were performed to obtain at least a partial Pentin-1 cDNA for probing the expression library. Information obtained from the sequencing of random cDNA clones from a *P. macroloba* immature seed library was used to generate a nascent codon usage table. The data obtained indicated the *P. macroloba* tree has no strong codon usage bias and that the GC content is moderate. A matrix of degenerate forward and reverse primers corresponding to Pentin-1 peptides were selected for use. The forward primer sequence was VVKRLAGYFDV (Pentin-1 amino acid Nos. 76–86: Val Val Lys Arg Leu Ala Gly Tyr Phe Asp Val) (SEQ ID NO:10) and the reverse primer sequence was ENMENLEK, (Pentin-1 amino acid Nos. 372–379: Glu Asn Met Glu Asn Leu Glu Lys) (SEQ ID NO:I 1). Due to the small amount of tissue available, the initial primer testing was conducted using genomic DNA derived from *P. macroloba* leaves. One of the sixty-four possible primer combinations yielded a 3.0 kb fragment which encoded the Pentin-1 peptide sequences. The forward and reverse primer pair were then used to amplify a 0.8 kb cDNA fragment from the total RNA isolated from mature (30–40 mm) seeds. Subsequent screening of the mature seed expression library with this 0.8 kb cDNA probe produced several related clones, one of which is a 1.4 kb clone that encodes twelve of the fifteen peptide sequences from Pentin-1 (SEQ ID NO:1).

Western blots were performed with Pentin-1, the Pentin-1 synthetic peptides, 5C9 and BSA proteins after exposure to selected antibodies. The blots were treated with a 1/10,000 dilution of antibodies raised against each of the peptides and 5C9. Each antibody recognized its antigen with no detectable cross-reactivity to BSA, the negative control. All the antibodies, except those raised against synthetic peptide number 1, recognized 1.0 micrograms of 5C9. Although the synthetic peptides KS and number 2 were 74% identical, anti-2 antibody did not recognize KS, but did detect Pentin-1 and 5C9.

The nucleic acid sequence of the Pentin-1 clone was determined by standard procedures known to those skilled in the art. The cDNA sequence and the predicted Pentin-1 protein sequence is provided in FIG. 1 and SEQ ID NO:1.

Bioassays of Cloned Material

Bioassays were conducted against Western corn rootworm (WCR) utilizing sonicated *E. coli* that had been transformed with one of several plasmids listed (Table 1). Transformed cells were grown in approximately 25–35 ml of TB broth. The cells were harvested after 24 h by centrifugation. The pellet was resuspended in approximately 1 ml of PBS buffer and sonicated. The resulting mixture was then top loaded onto the surface of diet and then infested with neonate WCR larvae. Mortality was recorded after four days. A positive result indicated 100% mortality. A negative result indicated mortality less than 10%. A similar experiment involved the use of transformed cells grown on an agar plate. The cells were scraped off after sufficient growth, suspended in a small amount of PBS buffer and then the solution was incorporated into the insect diet. A 4-day bioassay was also conducted with mortality recorded.

Table 1 displays the results of two replicated bioassays. All cells transformed with putative negative (non-lethal WCR genes) plasmids did not cause any larval mortality in either test. These plasmids are P7725, P88126, and P11426. The two plasmids that contain the coding sequence for Pentin-1, but not any promoters to produce the actual protein, PGEM and P11394 did not display any WCR activity. However, all plasmids containing the coding region for Pentin 1 (SEQ ID NO:1) and a functional expression cassette displayed excellent activity against WCR larvae. All such treatments had 100% mortality. Preliminary western blot analysis indicated that a protein similar in size to Pentin-1 was present in these cell extracts, but not in negative control samples. Activity was seen in both types of cell preparation and bioassays.

TABLE 1

| Plasmid # | Construct Content | Treatment | Bioassay Type | Bioassay Control Result | |
|---|---|---|---|---|---|
| P7725 | UBI-Bt | Broth Plate | microincorp top load | Negative | Neg. |
|  |  |  |  | Negative | Neg. |
| P8812 | Bt | Broth Plate | microincorp top load | Negative | Neg. |
|  |  |  |  | Negative | Neg. |
| moPentin/PGEM |  | Broth Plate | microincorp top load | Negative | Neg. |
|  |  |  |  | Negative | Neg. |
| P11184 | UBI-Full Pentin-1 cDNA from library clone-PinII | Broth Plate | microincorp top load | Positive | N/A |
|  |  |  |  | Positive | N/A |
| P11335 | UBI-Mod. Pentin (ATG-TGA)-PinII (modified from full clone, but | Broth Plate | microincorp top load | Positive | N/A |
|  |  |  |  | Positive | N/A |

TABLE 1-continued

| Plasmid # | Construct Content | Treatment | Bioassay Type | Bioassay Result | Bioassay Control Result |
|---|---|---|---|---|---|
| | not putative mature) | | | | |
| P11361 | Pentin-1 cDNA in pBK-CMV (lacZ promoter) | Broth Plate | microincorp top load | Positive | N/A |
| | | | | | N/A |
| P11394 | Pentin1 (mature protein) no promoter or Start codon) | Broth Plate | microincorp top load | Negative Negative | Neg. Neg. |
| P11426 | UBI-moPAT-CAMV35s | Broth Plate | microincorp top load | Negative Negative | Neg. Neg. |
| P11443 | Ubi-mopentin-1-Pin II/CAMV35S-Pat-CAMV35S | Broth Plate | micrincorp top load | Positive Positive | N/A N/A |

Transformation of Protoplasts Isolated from Corn Suspension Cells with Three Pentin-1 Gene Constructs for Gene Expression and for CRW Bioassay I. Protoplast Transformation Protocol Established Hill (GS3) suspension cells were used to make protoplasts. Cells were collected 3–4 days after subculture.

Cell digestion: Cells were digested in enzyme solution at 27° C. for 3–5 hours with 50–60 RPM shaking speed. The cell wall was digested with cellulase and pectolyase to release the protoplasts.

Harvesting of protoplasts: The digested material was passed through 30 mm filter and the protoplasts were recovered by centrifuging the filtrate at 1,000 RPM for 10 min.

The protoplast pellet was resuspended in 20 ml or 40 ml KMC solution. The protoplast density and total protoplast yield was determined by counting the number of protoplasts with a hemacytometer. The suspension was centrifuged to pellet the protoplasts. The protoplast pellet was suspended in MaMg transformation solution in a concentration of 2 million protoplasts per ml.

The solution in 2 ml quantities (about 4 million protoplasts) was dispensed into 15-ml round-bottom tubes. Each tube was a replication. At least three replications were used for each Pentin-1 gene construct. The constructs included both native Pentin-1 and the optimized Pentin-1 sequence. See SEQ ID NOS:1 and 3, respectively. Plasmid DNA was added to the protoplast suspension in the tubes (15 mg plasmid DNA/million protoplasts) and mixed.

After a five minute incubation, 2 ml 40% polyethylene glycol (PEG-8000, Sigma) was added to the protoplast/DNA mixture (the final PEG concentration is about 20%) and mixed by inverting tubes several times and incubated at room temperature for 20–30 min.

About 3 ml of W5 salt solution was added to each tube. The tubes were covered and gently inverted. This was repeated two times until the final volume was 13–14 ml. The suspension was centrifuged 8 min at 1,000 RPM. 3 ml FW medium was used to resuspend protoplasts. (See below). Using plastic squeeze Pasteur pipette, one treatment (3 ml) was dispensed into two wells of a 6-well culture plate, sealed with parafilm, and incubated 24–48 hours in the dark, at 28° C.

After culture, the protoplasts were transferred into a 15 ml tube using plastic squeeze Pasteur pipette and centrifuged 8 min at 500 RPM to pellet the protoplasts.

Protein analysis and Bioassay: One fifth to one quarter of the protoplast pellet in each replication for each transformation treatment was sampled for analysis of Pentin-1 expression by Western blot. The remainder of the protoplast pellet was used for bioassay. All replication samples from the same transformation treatment, that is transformed with the same Pentin-1 construct, were pooled and incorporated into diet for CRW bioassay. The bioassay results are provided in Table 2.

TABLE 2

The effect of Pentin-1, when expressed transiently in maize protoplasts, against WCR larvae. Data is a composite of 6 experiments replicated over time. Protoplasts were sonicated and the entire mixture was incorporated into the diet.

| Plasmid # | Construct Content | Western-Blot Analysis | Bioassay for Pentin | Control Mortality |
|---|---|---|---|---|
| P111841 | UBI-Full Pentin 1 cDNA from library clone-PinII | Positive | 32% | N/A |
| P11335 | UBI-Mod. Pentin (ATG-TGA)-PinII N/A (modified from full clone, but not putative mature) | Weak Positive | 0% | N/A |
| P11443 | Ubi-mopentin-1-Pin II/ | Strong Positive | 54% | N/A |
| P8126 | UBI-Bt | Negative | 0% | Negative Control |
| P3953 | UBI-Gus | Negative | 0% | Negative Control |

[1]P11184 was only used in the last 4 experiments.

II. Pentin-1 Gene Constructs for Transformation

P11184—Ubi promoter::Pentin-1 (original full-length clone)
P11335—Ubi promoter::Pentin-1 (partially modified gene)
P11443—Ubi promoter::moPentin-1 (optimized gene)

Solutions and Media Used for Transformation

KMC solution—1,000 ml

| KCl | 8.65 g |
|---|---|
| MgCl2—6H2O | 16.47 g |
| CaCl2—2H2O | 12.50 g |
| MES 0.5% | 5.0 g |
| PH 5.8 with KOH | |
| Filter sterilize | |

MaMg transformation solution—1,000 ml

| M mannitol | 108.1 g |
|---|---|
| 15 mM MgCl2—6H2O | 3.05 g |
| 10 mM MES | 1.95 g |
| PH 5.7 | |
| Filter sterilize | |

40% PEG—100 ml

Add 40 g PEG to 60 ml MaMg transformation solution. Briefly microwave to dissolve PEG. Add more MaMg solution to final volume of 100 ml. Adjust to pH 7.0. Filter sterilize.

Enzyme solution for digesting suspension cell (Enzyme solution)

Enzyme solution contains 3% cellulase RS and 0.3% pectolyase Y23 in protoplast solution.

Protoplast solution—1,000 ml

| M mannitol | 108.1 g |
|---|---|
| 10 mM MES | 1.95 g |
| 1 mM CaCl2—2H2O | 147 mg |
| 1 mM MgCl2—6H2O | 203 mg |
| 1% BSA (optional) | 1 g |
| PH 5.7 | |
| Filter sterilize | |

W5 salt solution—1,000 ml

| 154 mM NaCl | 9.0 g |
|---|---|
| 125 mM CaCl2—2H2O | 18.56 g |
| 5 mM KCl | 0.373 g |
| 5 mM Glucose | 0.901 g |
| PH 5.5 with KOH | |
| Filter sterilize | |

FW medium—1,000 ml

| MS salts (Sigma M5519) | 4.3 g |
|---|---|
| sucrose | 30.0 g |
| mannitol | 54.0 g |
| Proline | 1.5 g |
| 2,4-D | 3.0 mg |
| 1,000x B5 Vitamins | 1 ml |
| PH 5.8 | |
| Filter sterilize | |

Transformation and Regeneration of Maize Callus

Immature maize embryos from green house donor plants are bombarded with a plasmid containing the three Pentin-1 constructs plus a plasmid containing the selectable marker gene, PAT, (Wohlleben, W., Arnold, W., Broer, I., Hillemann, D., Strauch, E. and Puehler, A. "Nucleotide sequence of the phosphinothricin N-acetyltransferase gene from Streptomyces viridochromogenes Tue494 and its expression in *Nicotiana tabacum*" Gene 70:25–37 (1988) that confers resistance to the herbicide Bialophos by the following method: Please note: All media recipes are in the Appendix.

Preparation of target tissue: The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate. These are cultured on 560L medium 4 days prior to bombardment, in the dark. The day of bombardment, the embryos are transferred to 560Y medium for 4 hours, arranged within the 2.5 cm target zone.

Preparation of DNA:
100 µl prepared tungsten particles in water
10 µl (1 µg) DNA in TrisEDTA buffer (1 µg total)
100 µl 2.5 M CaCl2
10 µl 0.1 M spermidine Each reagent is added sequentially to the tungsten particle suspension, while maintained on the multi-tube vortexer. The plasmids are adjusted for a final 1:1 ratio by size. The final mixture is sonicated briefly, and allowed to incubate under constant vortexing for ten minutes. After the precipitation period, the tubes are centrifuged briefly, liquid removed, washed with 500 ml 100% ethanol, and centrifuged 30 seconds. Again the liquid is removed, and 105 µl 100% ethanol added to the final tungsten particle pellet. For particle gun bombardment, the tungsten/DNA particles are briefly sonicated and 10 µl spotted onto the center of each macro-carrier and allowed to dry about 2 minutes before bombardment.

Particle Gun Treatment: The sample plates are bombarded at level #4 in particle gun #HE34-1 or #HE34-2. All samples receive a single shot at 650 PSI, with a total of ten aliquots taken from each tube of prepared particles/DNA.

Subsequent treatment: Following bombardment, the embryos are kept on 560Y medium for 2 days then transferred to 560R selection medium containing 3 mg/liter Bialophos, and sub-cultured every 2 weeks. After approximately 10 weeks of selection, selection-resistant callus clones are sampled for PCR and fumonisin esterase TLC activity analysis. Positive lines are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

APPENDIX

| Ingredient | Amount | Unit |
|---|---|---|
| D-I $H_2O$ | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine.HCL 0.4 mg/ml | 0.500 | ml |
| L-Proline | 1.980 | g |
| Casein Hydrolystate (acid) | 0.300 | g |
| Sucrose | 20.000 | g |
| Glucose | 0.600 | g |
| 2,4-D 0.5 mg/ml | 1.600 | ml |
| Gelrite @ | 2.000 | g |
| Dicamba 1 mg/ml # | 1.200 | ml |
| Silver Nitrate 2 mg/ml # | 1.700 | ml |

Directions:
@=Add after bringing up to volume
=Add after sterilizing and cooling to temp.
Dissolve ingredients in polished D-I $H_2O$ in sequence Adjust to pH 5.8
Bring up to volume with polished D-I $H_2O$ after adjusting pH Sterilize and cool to 60° C.
=Dissolve 1.660 g of Calcium Chloride Dihydrate in 950.000 ml of polished D-I $H_2O$. Then dissolve 4.629 of Ammnonium Sulfate; 4.000 g of Potassium Phosphate Monobasic KH2PO4; 1.850 g of Magnesium Sulfate 7-$H_2O$, $MgSO_4$, 7H2O; and 28.300 g of Potassium Nitrate into sequence. Bring up to volume with polished D-I $H_2O$.
=Dissolve 3.000 g of Boric Acid; 10.000 g of Manganous Sulfate Monohydrate; 0.250 g of Sodium Molybdate Dihydrate; and 0.750 g of Potassium Iodide in polished D-I H$_2$O in sequence. Bring up to volume with polished D-I H$_2$O.

=Dissolve 3.700 g of Disodium EDTA Dihydrate and 2.790 g of Ferrous Sulfate 7-Hydrate into D-I H$_2$O. Bring up to volume with D-I H$_2$O.

Total Volume (L)=1.00

604 A

| Ingredient | Amount | Unit |
|---|---|---|
| D-I H$_2$O | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine.HCL 0.4 mg/ml | 0.500 | ml |
| L-Proline | 1.980 | g |
| Casein Hydrolysate (acid) | 0.300 | g |
| Sucrose | 20.000 | g |
| Glucose | 0.600 | g |
| 2, 4-D 0.5 mg/ml | 1.600 | ml |
| Gelrite @ | 2.000 | g |
| Dicamba 1 mg/ml # | 1.200 | ml |
| Silver Nitrate 2 mg/ml # | 1.700 | ml |
| Bialaphos 1 mg/ml # | 3.000 | ml |

Directions:
@=Add after bringing up to volume
=Add after sterilizing and cooling to temp.
Dissolve ingredients in polished D-I H$_2$O in sequence
Adjust to pH 5.8
Bring up to volume with polished D-I H$_2$O after adjusting pH
Sterilize and cool to 60° C.
=Dissolve 1.660 g of Calcium Chloride Dihydrate in 950.000 ml of polished D-I H$_2$O. Then dissolve 4.629 of Ammonium Sulfate; 4.000 g of Potassium Phosphate Monobasic KH2PO4; 1.850 g of Magnesium Sulfate 7-H$_2$O, MgSO$_4$, 7H$_2$O; and 28.300 g of Potassium Nitrate into sequence. Bring up to volume with polished D-I H$_2$O.
=Dissolve 3.000 g of Boric Acid; 10.000 g of Manganous Sulfate Monohydrate; 0.250 g of Sodium Molybdate Dihydrate; and 0.750 g of Potassium Iodide in polished D-I H$_2$O in sequence. Bring up to volume with polished D-I H$_2$O.
=Dissolve 3.700 g of Disodium EDTA Dihydrate and 2.790 g of Ferrous Sulfate 7-Hydrate into D-I H$_2$O. Bring up to volume with D-I H$_2$O.
Total Volume (L)=1.00

605 J

| Ingredient | Amount | Unit |
|---|---|---|
| D-I H$_2$O | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine.HCL 0.4 mg/ml | 0.500 | ml |
| Sucrose | 20.000 | g |
| Glucose | 0.600 | g |
| 2, 4-D 0.5 mg/ml | 1.600 | ml |
| Gelrite @ | 2.000 | g |
| Dicamba 1 mg/ml # | 1.200 | ml |
| Silver Nitrate 2 mg/ml # | 0.425 | ml |
| Bialaphos 1 mg/ml # | 3.000 | ml |

Directions:
@=Add after bringing up to volume
=Add after sterilizing and cooling to temp.
Dissolve ingredients in polished D-I H$_2$O in sequence
Adjust to pH 5.8
Bring up to volume with polished D-I H$_2$O after adjusting pH
Sterilize and cool to 60° C.
=Dissolve 1.660 g of Calcium Chloride Dihydrate in 950.000 ml of polished D-I H$_2$O. Then dissolve 4.629 of Ammonium Sulfate; 4.000 g of Potassium Phosphate Monobasic KH2PO4; 1.850 g of Magnesium Sulfate 7-H$_2$O, MgSO$_4$, 7H$_2$O; and 28.300 g of Potassium Nitrate into sequence. Bring up to volume with polished D-I H$_2$O.
=Dissolve 3.000 g of Boric Acid; 10.000 g of Manganous Sulfate Monohydrate; 0.250 g of Sodium Molybdate Dihydrate; and 0.750 g of Potassium Iodide in polished D-I H$_2$O in sequence. Bring up to volume with polished D-I H$_2$O.
=Dissolve 3.700 g of Disodium EDTA Dihydrate and 2.790 g of Ferrous Sulfate 7-Hydrate into D-I H$_2$O. Bring up to volume with D-I H$_2$O.
Total Volume (L)=1.00

604S

| Ingredient | Amount | Unit |
|---|---|---|
| D-I H$_2$O | 800.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine.HCL 0.4 mg/ml | 0.500 | ml |
| L-Proline | 1.980 | g |
| Casein Hydrolysate (acid) | 0.300 | g |
| Sucrose | 120.000 | g |
| Glucose | 0.600 | g |
| 2, 4-D 0.5 mg/ml | 1.600 | ml |
| Gelrite # | 2.000 | g |
| Dicamba 1 mg/ml # | 1.200 | ml |
| Silver Nitrate 2 mg/ml # | 1.700 | ml |

Directions:
@=Add after bringing up to volume
=Add after sterilizing and cooling to temp.
Dissolve ingredients in polished D-I H$_2$O in sequence
Adjust to pH 5.8
Bring up to volume with polished D-I H$_2$O after adjusting pH
Sterilize and cool to 60° C.
=Dissolve 1.660 g of Calcium Chloride Dihydrate in 950.000 ml of polished D-I H$_2$O. Then dissolve 4.629 of Ammonium Sulfate; 4.000 g of Potassium Phosphate Monobasic KH2PO4; 1.850 g of Magnesium Sulfate 7-H$_2$O, MgSO$_4$, 7H$_2$O; and 28.300 g of Potassium Nitrate into sequence. Bring up to volume with polished D-I H$_2$O.
=Dissolve 3.000 g of Boric Acid; 10.000 g of Manganous Sulfate Monohydrate; 0.250 g of Sodium Molybdate Dihydrate; and 0.750 g of Potassium Iodide in 950.000 ml of polished D-I H$_2$O in sequence. Bring up to volume with polished D-I H$_2$O.
=Dissolve 3.700 g of Disodium EDTA Dihydrate and 2.790 g of Ferrous Sulfate 7-Hydrate into 950.000 ml of D-I H$_2$O. Bring up to volume with D-I H$_2$O.
Total Volume (L)=1.00

| 272V | | |
|---|---|---|
| Ingredient | Amount | Unit |
| D-I H$_2$O | 950.000 | ml |
| MS Salts (GIBCO 11117-074) | 4.300 | g |
| Myo-Inositol | 0.100 | g |
| MS Vitamins Stock Solution ## | 5.000 | ml |
| Sucrose | 40.000 | g |
| Bacto-Agar @ | 6.000 | g |

Directions:
@=Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
=Dissolve 0.100 g of Nicotinic Acid; 0.020 g of Thiamine.HCL; 0.100 g of Pyridoxine.HCL; and 0.400 g of Glycine in 875.00 ml of polished D-I H2O in sequence. Bring up to volume with polished D-I H$_2$O. Make in 400 ml portions. Thiamine.HCL & Pyridoxine.HCL are in Dark Descicator. Store for one month, unless contamination or precipitation occur, then make fresh stock.
Total Volume (L)=1.00

| 288J | | |
|---|---|---|
| Ingredient | Amount | Unit |
| D-I H$_2$O | 950.000 | ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indole Acetic Acid 0.5 mg/ml # | 2.000 | ml |
| .1 mM Absissic Acid | 1.000 | ml |
| Bialaphos 1 mg/ml # | 3.000 | ml |

Directions:
@=Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
Add 3.5 g/L of Gelrite for cell biology.
=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Descicator. Store for one month, unless contamination or precipitation occur, then make fresh stock.
Total Volume (L)=1.00

| 560L | | |
|---|---|---|
| Ingredient | Amount | Unit |
| D-I Water, Filtered | 950.000 | ml |
| CHU (N6) Basal Salts (SIGMA C-1416) | 4.000 | g |
| Eriksson's Vitamin Mix (1000X SIGMA-1511 | 0.400 | ml |
| Thiamine.HCL 0.4 mg/ml | 1.250 | ml |
| Sucrose | 20.000 | g |
| 2, 4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@=Add after bringing up to volume
=Add after sterilizing and cooling to temp.
Dissolve ingredients in D-I H$_2$O in sequence
Adjust to pH 5.8 with KOH
Bring up to volume with D-I H$_2$O
Sterilize and cool to room temp.
Total Volume (L)=1.00

| 560R | | |
|---|---|---|
| Ingredient | Amount | Unit |
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 30.000 | g |
| 2, 4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:
@=Add after bringing up to volume
=Add after sterilizing and cooling to temp.
Dissolve ingredients in D-I H$_2$O in sequence
Adjust to pH 5.8 with KOH
Bring up to volume with D-I H$_2$O
Sterilize and cool to room temp.
Total Volume (L)=1.00

| 560Y | | |
|---|---|---|
| Ingredient | Amount | Unit |
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 120.000 | g |
| 2, 4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@=Add after bringing up to volume
=Add after sterilizing and cooling to temp.
Dissolve ingredients in D-I H$_2$O in sequence Adjust to pH 5.8 with KOH
Bring up to volume with D-I H₂O
Sterilize and cool to room temp.
 Autoclave less time because of increased sucrose
Total Volume (L)=1.00

Plasmids PHP 11361 and PHP 11511 were deposited with the American Type Culture Collection, Bethesda, Md., and given Accession Nos. 209026 and 209025, respectively. PHP11361 comprises the nucleotide sequence of the native Pentin-1 sequence. PHP11511 comprises the optimized Pentin-1 sequence. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1469 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Pentaclethra macroloba (ix) FEATURE:
      (A) NAME/KEY: CDS
      (B) LOCATION: 31..1257

(xi) SEQUENCE DESCRIPTION: SEQ ID NO:1:

```
CGGCACGAGC TCGTACAGAT TCTATCCATT ATG AAG TCG AAA ATG GCC ATG CTC        54
                                Met Lys Ser Lys Met Ala Met Leu
                                 1               5

CTT TTG TTA TTT TGT GTG TTA TCT AAT CAG CTA GTG GCA GCA TTT TCC        102
Leu Leu Leu Phe Cys Val Leu Ser Asn Gln Leu Val Ala Ala Phe Ser
    10                  15                  20

ACA CAA GCG AAA GCT TCT AAA GAT GGA AAC TTA GTC ACA GTT CTT GCC        150
Thr Gln Ala Lys Ala Ser Lys Asp Gly Asn Leu Val Thr Val Leu Ala
 25                  30                  35                  40

ATT GAT GGA GGT GGT ATC AGA GGA ATT ATC CCC GGA GTT ATT CTC AAA        198
Ile Asp Gly Gly Gly Ile Arg Gly Ile Ile Pro Gly Val Ile Leu Lys
                 45                  50                  55

CAA CTA GAA GCT ACT CTT CAG AGA TGG GAC TCA AGT GCA AGA CTA GCA        246
Gln Leu Glu Ala Thr Leu Gln Arg Trp Asp Ser Ser Ala Arg Leu Ala
             60                  65                  70

GAG TAT TTT GAT GTG GTT GCC GGG ACG AGC ACT GGA GGG ATT ATA ACT        294
Glu Tyr Phe Asp Val Val Ala Gly Thr Ser Thr Gly Gly Ile Ile Thr
         75                  80                  85

GCC ATT CTA ACT GCC CCG GAC CCA CAA AAC AAG GAC CGT CCT TTG TAT        342
Ala Ile Leu Thr Ala Pro Asp Pro Gln Asn Lys Asp Arg Pro Leu Tyr
     90                  95                 100

GCT GCC GAA GAA ATT ATC GAC TTC TAC ATA GAG CAT GGT CCT TCC ATT        390
Ala Ala Glu Glu Ile Ile Asp Phe Tyr Ile Glu His Gly Pro Ser Ile
105                 110                 115                 120

TTT AAT AAA TCC ACC GCC TGC TCG TTG CCT GGT ATC TTT TGT CCA AAG        438
Phe Asn Lys Ser Thr Ala Cys Ser Leu Pro Gly Ile Phe Cys Pro Lys
                125                 130                 135

TAT GAT GGG AAG TAT TTA CAA GAA ATA ATA AGC CAG AAA TTG AAT GAA        486
```

```
Tyr Asp Gly Lys Tyr Leu Gln Glu Ile Ile Ser Gln Lys Leu Asn Glu
            140                 145                 150

ACA CTA CTA GAC CAG ACA ACA ACA AAT GTT GTT ATC CCT TCC TTC GAC        534
Thr Leu Leu Asp Gln Thr Thr Thr Asn Val Val Ile Pro Ser Phe Asp
            155                 160                 165

ATC AAG CTT CTT CGT CCA ACC ATA TTC TCA ACT TTC AAG TTA GAG GAA        582
Ile Lys Leu Leu Arg Pro Thr Ile Phe Ser Thr Phe Lys Leu Glu Glu
170                 175                 180

GTT CCT GAG TTA AAT GTC AAA CTC TCC GAT GTA TGC ATG GGA ACT TCA        630
Val Pro Glu Leu Asn Val Lys Leu Ser Asp Val Cys Met Gly Thr Ser
185                 190                 195                 200

GCA GCA CCA ATC GTA TTT CCT CCC TAT TAT TTC AAG CAT GGA GAT ACT        678
Ala Ala Pro Ile Val Phe Pro Pro Tyr Tyr Phe Lys His Gly Asp Thr
            205                 210                 215

GAA TTC AAT CTC GTT GAT GGT GCA ATC ATC GCT GAT ATT CCG GCC CCG        726
Glu Phe Asn Leu Val Asp Gly Ala Ile Ile Ala Asp Ile Pro Ala Pro
            220                 225                 230

GTT GCT CTC AGC GAG GTG CTC CAG CAA GAA AAA TAC AAG AAT AAA GAA        774
Val Ala Leu Ser Glu Val Leu Gln Gln Glu Lys Tyr Lys Asn Lys Glu
            235                 240                 245

ATC CTT TTG CTG TCT ATA GGA ACT GGA GTT GTA AAA CCT GGT GAG GGT        822
Ile Leu Leu Leu Ser Ile Gly Thr Gly Val Val Lys Pro Gly Glu Gly
            250                 255                 260

TAT TCT GCT AAT CGT ACT TGG ACT ATT TTC GAT TGG AGT AGT GAA ACT        870
Tyr Ser Ala Asn Arg Thr Trp Thr Ile Phe Asp Trp Ser Ser Glu Thr
265                 270                 275                 280

TTA ATC GGG CTT ATG GGT CAT GGA ACG AGA GCC ATG TCT GAT TAT TAC        918
Leu Ile Gly Leu Met Gly His Gly Thr Arg Ala Met Ser Asp Tyr Tyr
                285                 290                 295

GTT GGC TCA CAT TTC AAA GCC CTT CAA CCC CAG AAT AAC TAC CTC CGA        966
Val Gly Ser His Phe Lys Ala Leu Gln Pro Gln Asn Asn Tyr Leu Arg
            300                 305                 310

ATT CAG GAA TAC GAT TTA GAT CCG GCA CTG GAA AGC ATT GAT GAT GCT       1014
Ile Gln Glu Tyr Asp Leu Asp Pro Ala Leu Glu Ser Ile Asp Asp Ala
            315                 320                 325

TCA ACG GAA AAC ATG GAG AAT CTG GAA AAG GTA GGA CAG AGT TTG TTG       1062
Ser Thr Glu Asn Met Glu Asn Leu Glu Lys Val Gly Gln Ser Leu Leu
            330                 335                 340

AAC GAA CCA GTT AAA AGG ATG AAT CTG AAT ACT TTT GTC GTT GAA GAA       1110
Asn Glu Pro Val Lys Arg Met Asn Leu Asn Thr Phe Val Val Glu Glu
345                 350                 355                 360

ACA GGT GAA GGT ACC AAT GCA GAA GCT TTA GAC AGG CTG GCT CAG ATT       1158
Thr Gly Glu Gly Thr Asn Ala Glu Ala Leu Asp Arg Leu Ala Gln Ile
                365                 370                 375

CTT TAT GAA GAA AAG ATT ACT CGT GGT CTC GGA AAG ATA TCT TTG GAA       1206
Leu Tyr Glu Glu Lys Ile Thr Arg Gly Leu Gly Lys Ile Ser Leu Glu
            380                 385                 390

GTG GAT AAC ATT GAT CCA TAT ACT GAA CGT GTT AGG AAA CTG CTA TTC       1254
Val Asp Asn Ile Asp Pro Tyr Thr Glu Arg Val Arg Lys Leu Leu Phe
            395                 400                 405

TGA TACGAATTGA AGTTGTTTCC TCCTTGCCAT ATAGCCTCAC TTTGTTTGGC            1307
 *

AATAAATAAA TAAATAAATG TAATCGTTTG GTTTGATGTC CTTGACTTTG TCATATATGC     1367

TGGCTCTATA AGAAGCACCA GCAGATAAAT AAAGGTTAAT GTTTGAGGTA TWAARWAAAA     1427

AAAAAAAAAA AAAAAAAAAA AAAAAAAAAA AAAAAACTC GA                        1469

(2) INFORMATION FOR SEQ ID NO:2:
```

```
    (i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Ser Lys Met Ala Met Leu Leu Leu Phe Cys Val Leu Ser
 1               5                  10                  15

Asn Gln Leu Val Ala Ala Phe Ser Thr Gln Ala Lys Ala Ser Lys Asp
                20                  25                  30

Gly Asn Leu Val Thr Val Leu Ala Ile Asp Gly Gly Ile Arg Gly
                35                  40                  45

Ile Ile Pro Gly Val Ile Leu Lys Gln Leu Glu Ala Thr Leu Gln Arg
 50                  55                  60

Trp Asp Ser Ser Ala Arg Leu Ala Glu Tyr Phe Asp Val Val Ala Gly
 65                  70                  75                  80

Thr Ser Thr Gly Gly Ile Ile Thr Ala Ile Leu Thr Ala Pro Asp Pro
                85                  90                  95

Gln Asn Lys Asp Arg Pro Leu Tyr Ala Ala Glu Glu Ile Ile Asp Phe
                100                 105                 110

Tyr Ile Glu His Gly Pro Ser Ile Phe Asn Lys Ser Thr Ala Cys Ser
                115                 120                 125

Leu Pro Gly Ile Phe Cys Pro Lys Tyr Asp Gly Lys Tyr Leu Gln Glu
                130                 135                 140

Ile Ile Ser Gln Lys Leu Asn Glu Thr Leu Leu Asp Gln Thr Thr Thr
145                 150                 155                 160

Asn Val Val Ile Pro Ser Phe Asp Ile Lys Leu Leu Arg Pro Thr Ile
                165                 170                 175

Phe Ser Thr Phe Lys Leu Glu Glu Val Pro Glu Leu Asn Val Lys Leu
                180                 185                 190

Ser Asp Val Cys Met Gly Thr Ser Ala Ala Pro Ile Val Phe Pro Pro
                195                 200                 205

Tyr Tyr Phe Lys His Gly Asp Thr Glu Phe Asn Leu Val Asp Gly Ala
                210                 215                 220

Ile Ile Ala Asp Ile Pro Ala Pro Val Ala Leu Ser Glu Val Leu Gln
225                 230                 235                 240

Gln Glu Lys Tyr Lys Asn Lys Glu Ile Leu Leu Leu Ser Ile Gly Thr
                245                 250                 255

Gly Val Val Lys Pro Gly Glu Gly Tyr Ser Ala Asn Arg Thr Trp Thr
                260                 265                 270

Ile Phe Asp Trp Ser Ser Glu Thr Leu Ile Gly Leu Met Gly His Gly
                275                 280                 285

Thr Arg Ala Met Ser Asp Tyr Tyr Val Gly Ser His Phe Lys Ala Leu
                290                 295                 300

Gln Pro Gln Asn Asn Tyr Leu Arg Ile Gln Glu Tyr Asp Leu Asp Pro
305                 310                 315                 320

Ala Leu Glu Ser Ile Asp Asp Ala Ser Thr Glu Asn Met Glu Asn Leu
                325                 330                 335

Glu Lys Val Gly Gln Ser Leu Leu Asn Glu Pro Val Lys Arg Met Asn
                340                 345                 350

Leu Asn Thr Phe Val Val Glu Glu Thr Gly Gly Thr Asn Ala Glu
                355                 360                 365

Ala Leu Asp Arg Leu Ala Gln Ile Leu Tyr Glu Glu Lys Ile Thr Arg
```

```
                370              375              380
Gly Leu Gly Lys Ile Ser Leu Glu Val Asp Asn Ile Asp Pro Tyr Thr
385              390              395              400

Glu Arg Val Arg Lys Leu Leu Phe
                405
```

(2) INFORMATION FOR SEQ ID NO:3:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "cDNA of Pentin-1 optimized
            for enhanced expression"

(vi) ORIGINAL SOURCE:
        (A) ORGANISM: Pentaclethra macroloba (ix) FEATURE:
        (A) NAME/KEY: CDS
        (B) LOCATION: 1..1227

(xi) SEQUENCE DESCRIPTION: SEQ ID NO:3:

```
ATG AAG TCC AAG ATG GCC ATG CTC CTC CTC CTC TTC TGC GTG CTC TCC      48
Met Lys Ser Lys Met Ala Met Leu Leu Leu Leu Phe Cys Val Leu Ser
410              415              420              425

AAC CAG CTC GTG GCC GCG TTC TCC ACC CAG GCC AAG GCC TCC AAG GAC      96
Asn Gln Leu Val Ala Ala Phe Ser Thr Gln Ala Lys Ala Ser Lys Asp
                430              435              440

GGC AAC CTC GTG ACC GTG CTC GCC ATC GAC GGC GGC GGC ATC CGC GGC     144
Gly Asn Leu Val Thr Val Leu Ala Ile Asp Gly Gly Gly Ile Arg Gly
                445              450              455

ATC ATC CCG GGC GTG ATC CTC AAG CAG CTC GAG GCG ACC CTC CAG AGG     192
Ile Ile Pro Gly Val Ile Leu Lys Gln Leu Glu Ala Thr Leu Gln Arg
            460              465              470

TGG GAC TCC AGC GCC AGG CTC GCG GAG TAC TTC GAC GTG GTG GCC GGC     240
Trp Asp Ser Ser Ala Arg Leu Ala Glu Tyr Phe Asp Val Val Ala Gly
            475              480              485

ACC TCC ACC GGC GGC ATC ATC ACC GCC ATC CTC ACC GCC CCG GAC CCG     288
Thr Ser Thr Gly Gly Ile Ile Thr Ala Ile Leu Thr Ala Pro Asp Pro
490              495              500              505

CAG AAC AAG GAC CGC CCG CTC TAC GCC GCC GAG GAG ATC ATC GAC TTC     336
Gln Asn Lys Asp Arg Pro Leu Tyr Ala Ala Glu Glu Ile Ile Asp Phe
                510              515              520

TAC ATC GAG CAC GGC CCG TCC ATC TTC AAC AAG TCC ACC GCC TGC TCC     384
Tyr Ile Glu His Gly Pro Ser Ile Phe Asn Lys Ser Thr Ala Cys Ser
                525              530              535

CTC CCG GGC ATC TTC TGC CCG AAG TAC GAC GGC AAG TAC CTC CAG GAG     432
Leu Pro Gly Ile Phe Cys Pro Lys Tyr Asp Gly Lys Tyr Leu Gln Glu
                540              545              550

ATC ATC TCC CAG AAG CTC AAC GAG ACC CTC CTC GAC CAG ACC ACC ACC     480
Ile Ile Ser Gln Lys Leu Asn Glu Thr Leu Leu Asp Gln Thr Thr Thr
                555              560              565

AAC GTG GTG ATC CCG TCC TTC GAC ATC AAG CTC CTC CGC CCG ACC ATC     528
Asn Val Val Ile Pro Ser Phe Asp Ile Lys Leu Leu Arg Pro Thr Ile
570              575              580              585

TTC TCC ACC TTC AAG CTC GAG GAG GTG CCG GAG CTC AAC GTG AAG CTC     576
Phe Ser Thr Phe Lys Leu Glu Glu Val Pro Glu Leu Asn Val Lys Leu
                590              595              600

TCC GAC GTG TGC ATG GGC ACC TCC GCC GCC CCG ATC GTG TTC CCG CCG     624
```

-continued

```
Ser Asp Val Cys Met Gly Thr Ser Ala Ala Pro Ile Val Phe Pro Pro
        605                 610                 615

TAC TAC TTC AAG CAC GGC GAC ACC GAG TTC AAC CTC GTC GAC GGC GCG      672
Tyr Tyr Phe Lys His Gly Asp Thr Glu Phe Asn Leu Val Asp Gly Ala
            620                 625                 630

ATC ATC GCG GAC ATC CCA GCC CCG GTG GCC CTC TCC GAG GTG CTC CAG      720
Ile Ile Ala Asp Ile Pro Ala Pro Val Ala Leu Ser Glu Val Leu Gln
635                 640                 645

CAG GAG AAG TAC AAG AAC AAG GAG ATC CTC CTC CTG AGC ATC GGC ACC      768
Gln Glu Lys Tyr Lys Asn Lys Glu Ile Leu Leu Leu Ser Ile Gly Thr
650                 655                 660                 665

GGC GTG GTG AAG CCG GGC GAG GGC TAC TCC GCC AAC CGC ACC TGG ACC      816
Gly Val Val Lys Pro Gly Glu Gly Tyr Ser Ala Asn Arg Thr Trp Thr
                670                 675                 680

ATC TTC GAC TGG TCC TCC GAG ACC CTC ATC GGC CTC ATG GGG CAC GGC      864
Ile Phe Asp Trp Ser Ser Glu Thr Leu Ile Gly Leu Met Gly His Gly
            685                 690                 695

ACC CGC GCC ATG TCC GAC TAC TAC GTG GGC TCC CAC TTC AAG GCC CTC      912
Thr Arg Ala Met Ser Asp Tyr Tyr Val Gly Ser His Phe Lys Ala Leu
        700                 705                 710

CAG CCG CAG AAC AAC TAC CTC CGC ATC CAG GAG TAC GAC CTC GAC CCG      960
Gln Pro Gln Asn Asn Tyr Leu Arg Ile Gln Glu Tyr Asp Leu Asp Pro
715                 720                 725

GCC CTC GAG TCC ATC GAC GAC GCC TCC ACC GAG AAC ATG GAG AAC CTC     1008
Ala Leu Glu Ser Ile Asp Asp Ala Ser Thr Glu Asn Met Glu Asn Leu
730                 735                 740                 745

GAG AAG GTG GGC CAG TCC CTC CTC AAC GAG CCG GTG AAG CGC ATG AAC     1056
Glu Lys Val Gly Gln Ser Leu Leu Asn Glu Pro Val Lys Arg Met Asn
                750                 755                 760

CTC AAC ACG TTC GTC GTG GAG GAG ACC GGC GAG GGG ACC AAC GCC GAG     1104
Leu Asn Thr Phe Val Val Glu Glu Thr Gly Glu Gly Thr Asn Ala Glu
            765                 770                 775

GCG CTC GAC CGC CTC GCC CAG ATC CTC TAC GAG GAG AAG ATC ACC CGC     1152
Ala Leu Asp Arg Leu Ala Gln Ile Leu Tyr Glu Glu Lys Ile Thr Arg
        780                 785                 790

GGC CTC GGC AAG ATC TCC CTC GAG GTG GAC AAC ATC GAC CCG TAC ACC     1200
Gly Leu Gly Lys Ile Ser Leu Glu Val Asp Asn Ile Asp Pro Tyr Thr
795                 800                 805

GAG CGC GTG CGC AAG CTC CTC TTC TGA                                 1227
Glu Arg Val Arg Lys Leu Leu Phe  *
810                 815

(2) INFORMATION FOR SEQ ID NO:4:

(i) SEQUENCE CHARACTERISTICS:
        (A) LENGTH:  408 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Ser Lys Met Ala Met Leu Leu Leu Leu Phe Cys Val Leu Ser
  1               5                  10                  15

Asn Gln Leu Val Ala Ala Phe Ser Thr Gln Ala Lys Ala Ser Lys Asp
             20                  25                  30

Gly Asn Leu Val Thr Val Leu Ala Ile Asp Gly Gly Ile Arg Gly
         35                  40                  45

Ile Ile Pro Gly Val Ile Leu Lys Gln Leu Glu Ala Thr Leu Gln Arg
 50                  55                  60
```

-continued

```
Trp Asp Ser Ser Ala Arg Leu Ala Glu Tyr Phe Asp Val Val Ala Gly
 65                  70                  75                  80

Thr Ser Thr Gly Gly Ile Ile Thr Ala Ile Leu Thr Ala Pro Asp Pro
                 85                  90                  95

Gln Asn Lys Asp Arg Pro Leu Tyr Ala Ala Glu Glu Ile Ile Asp Phe
            100                 105                 110

Tyr Ile Glu His Gly Pro Ser Ile Phe Asn Lys Ser Thr Ala Cys Ser
        115                 120                 125

Leu Pro Gly Ile Phe Cys Pro Lys Tyr Asp Gly Lys Tyr Leu Gln Glu
    130                 135                 140

Ile Ile Ser Gln Lys Leu Asn Glu Thr Leu Leu Asp Gln Thr Thr Thr
145                 150                 155                 160

Asn Val Val Ile Pro Ser Phe Asp Ile Lys Leu Leu Arg Pro Thr Ile
                165                 170                 175

Phe Ser Thr Phe Lys Leu Glu Glu Val Pro Glu Leu Asn Val Lys Leu
            180                 185                 190

Ser Asp Val Cys Met Gly Thr Ser Ala Ala Pro Ile Val Phe Pro Pro
        195                 200                 205

Tyr Tyr Phe Lys His Gly Asp Thr Glu Phe Asn Leu Val Asp Gly Ala
    210                 215                 220

Ile Ile Ala Asp Ile Pro Ala Pro Val Ala Leu Ser Glu Val Leu Gln
225                 230                 235                 240

Gln Glu Lys Tyr Lys Asn Lys Glu Ile Leu Leu Ser Ile Gly Thr
                245                 250                 255

Gly Val Val Lys Pro Gly Glu Gly Tyr Ser Ala Asn Arg Thr Trp Thr
                260                 265                 270

Ile Phe Asp Trp Ser Ser Glu Thr Leu Ile Gly Leu Met Gly His Gly
        275                 280                 285

Thr Arg Ala Met Ser Asp Tyr Tyr Val Gly Ser His Phe Lys Ala Leu
    290                 295                 300

Gln Pro Gln Asn Asn Tyr Leu Arg Ile Gln Glu Tyr Asp Leu Asp Pro
305                 310                 315                 320

Ala Leu Glu Ser Ile Asp Asp Ala Ser Thr Glu Asn Met Glu Asn Leu
                325                 330                 335

Glu Lys Val Gly Gln Ser Leu Leu Asn Glu Pro Val Lys Arg Met Asn
            340                 345                 350

Leu Asn Thr Phe Val Val Glu Glu Thr Gly Gly Thr Asn Ala Glu
        355                 360                 365

Ala Leu Asp Arg Leu Ala Gln Ile Leu Tyr Glu Glu Lys Ile Thr Arg
    370                 375                 380

Gly Leu Gly Lys Ile Ser Leu Glu Val Asp Asn Ile Asp Pro Tyr Thr
385                 390                 395                 400

Glu Arg Val Arg Lys Leu Leu Phe
                405
```

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Pentaclethra macroloba (xi) SEQUENCE DESCRIPTION: SEQ ID NO:5:

Met Ser Thr Ser Ala Ala Pro Ile Val Phe Pro Pro Tyr Tyr Phe Lys
1               5                   10                  15

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Pentaclethra macroloba (xi) SEQUENCE DESCRIPTION: SEQ ID NO:6:

Ala Leu Gln Pro Gln Asn Asn Tyr Leu Arg Gln Glu Tyr Asp Leu Asp
1               5                   10                  15

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Pentaclethra macroloba (xi) SEQUENCE DESCRIPTION: SEQ ID NO:7:

Pro Asp Trp Val Val Ile Arg Ser Gln Ser Val Gly Lys
1               5                   10

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Pentaclethra macroloba (xi) SEQUENCE DESCRIPTION: SEQ ID NO:8:

Lys Ala Phe Val Asn Gly Val Tyr Phe Ile Asn Thr Tyr Asp Ser Ala
1               5                   10                  15

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Pentaclethra macroloba (xi) SEQUENCE DESCRIPTION: SEQ ID NO:9:

-continued

```
Asn Asn Tyr Leu Arg Ile Gln Glu Tyr Asp Leu Pro Pro Ala Leu
1               5                   10                  15

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Pentaclethra macroloba (xi) SEQUENCE DESCRIPTION: SEQ ID NO:10:

Val Val Lys Arg Leu Ala Gly Tyr Phe Asp Val
1               5                   10

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Pentaclethra macroloba (xi) SEQUENCE DESCRIPTION: SEQ ID NO:11:

Glu Asn Met Glu Asn Leu Glu Lys
1               5
```

What is claimed is:

1. An isolated nucleotide sequence encoding a polypeptide having insecticidal activity for corn rootworm, said molecule having a sequence selected from the group consisting of:
   (a) the sequence set forth in SEQ ID NO: 1;
   (b) nucleotide sequences which hybridize to the sequence set forth in SEQ ID NO:1 under stringent conditions defined by a wash stringency of 0.3M NaCl, 0.03 M sodium citrate, 0.1% SDS at 70° C.;
   (c) nucleotide sequences which encode the amino acid sequence set forth in SEQ ID NO:2; and
   (d) nucleotide sequences which encode a Pentin-1 polypeptide from Pentaclethra.

2. The isolated nucleotide sequence of claim 1, which encodes the protein set forth in SEQ ID NO:2.

3. The nucleotide sequence of claim 1, wherein said nucleotide sequence is the sequence set forth in SEQ ID NO:1.

4. The nucleotide sequence of claim 1, wherein said sequence is synthetic.

5. The nucleotide sequence of claim 1, wherein said sequence has been optimized for expression in maize.

6. A plant which has been stably transformed with an expression cassette comprising a promoter that drives expression in a plant cell operably linked to the nucleotide sequence of claim 1.

7. The plant of claim 6, wherein said plant is maize.

8. Seed of the plant of claim 6 or 7.

9. The plant of claim 6 wherein said nucleotide sequence encodes the amino acid sequence set forth in SEQ ID NO:2.

10. The plant of claim 6, wherein said nucleotide sequence is the sequence set forth in SEQ ID NO:1.

11. The plant of claim 6, wherein said nucleotide sequence is operably linked to a root preferential promoter.

12. The plant of claim 9, wherein said nucleotide sequence is operably linked to a root preferential promoter.

13. The plant of claim 10, wherein said nucleotide sequence is operably linked to a root preferential promoter.

14. A method for controlling corn rootworm said method comprising: transforming a plant cell with an expression cassette comprising a promoter that drives expression in a plant cell operably linked to the nucleotide sequence of claim 1, and regenerating a transformed plant from said plant cell.

15. A. The method of claim 14, wherein said promoter is a root preferential promoter.

16. The method of claim 15, wherein said nucleotide sequence encodes the amino acid sequence set forth in SEQ ID NO:2.

17. The method of claim 15, wherein said plant cell is from a monocot.

18. The method of claim 17, wherein said monocot is maize.

19. A plant cell that has been stably transformed with an expression cassette comprising a promoter that drives expression in a plant cell operably linked to the nucleotide sequence of claim 1.

20. The plant cell of claim 19, wherein said promoter is a root preferential promoter.

21. The plant cell of claim 20, wherein said nucleotide sequence encodes the amino acid sequence set forth in SEQ ID NO:2.

22. The plant cell of claim 20, wherein said plant cell is from a monocot.

23. The plant cell of claim 22, wherein said monocot is maize.

24. A vector comprising the nucleotide sequence of claim 1.

25. A plant or microorganism which has been transformed with the vector of claim 24.

26. An isolated nucleotide sequence comprising a polynucleotide having at least 90% sequence identity with SEQ ID NO:1, wherein the percent sequence identity is determined according to the GAP program in the Wisconsin Genetics Software Package, using the default settings.

* * * * *

UNITED STATES PATENT AND TRADEMARK OFFICE
CERTIFICATE OF CORRECTION

PATENT NO. : 6,057,491
DATED : May 2, 2000
INVENTOR(S) : Cigan et al.

It is certified that error appears in the above-identified patent and that said Letters Patent is hereby corrected as shown below:

Title page, item [54], line 1 and Column 1, line 1:
In the title, "PROTEIN" should read --PROTEINS--.

Title page, item [73], in the first Assignee's name, "Borad" should read --Board--.

Title page, [56] References Cited:
FOREIGN PATENT DOCUMENTS, line 1, "WIPO" should read --Canada--.
OTHER PUBLICATIONS, line 11, "vol. 38" should read --vol. 28--; line 27, "*Alcasia*" should read --*Alocasia*--; after "Chamissonis," insert a quotation mark ("); line 28, cancel the quotation mark before "Phytochemistry".

Column 45, line 51, "Pentaclethra" should read --*Pentaclethra*--.

Signed and Sealed this

Sixth Day of March, 2001

Attest:

NICHOLAS P. GODICI

Attesting Officer     Acting Director of the United States Patent and Trademark Office